US011833056B2

(12) United States Patent
Kemp et al.

(10) Patent No.: US 11,833,056 B2
(45) Date of Patent: Dec. 5, 2023

(54) STEMLESS METAPHYSEAL HUMERAL IMPLANT

(71) Applicant: Howmedica Osteonics Corp., Mahwah, NJ (US)

(72) Inventors: Philip T. Kemp, White Plains, NY (US); Andrew J. Nelson, New City, NY (US); Jan Heinsohn, Hoboken, NJ (US); Rajan Yadav, New Delhi (IN); Koustubh Rao, Davie, FL (US); Gennaro A. Barile, Secaucus, NJ (US); Ashish Mehta, Rajasthan (IN); Venkateswaran Perumal, Gurgaon (IN); David Viscardi, Glen Rock, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 17/557,334

(22) Filed: Dec. 21, 2021

(65) Prior Publication Data

US 2022/0110756 A1 Apr. 14, 2022

Related U.S. Application Data

(63) Continuation of application No. 17/372,600, filed on Jul. 12, 2021, which is a continuation of application
(Continued)

(51) Int. Cl.
*A61F 2/40* (2006.01)
*A61F 2/46* (2006.01)
*A61F 2/30* (2006.01)

(52) U.S. Cl.
CPC .......... *A61F 2/4003* (2013.01); *A61F 2/4014* (2013.01); *A61F 2/4081* (2013.01);
(Continued)

(58) Field of Classification Search
CPC .... A61F 2/4003; A61F 2/4014; A61F 2/4081; A61F 2/4612; A61F 2/4637; A61F 2002/4007; A61F 2002/4018
See application file for complete search history.

(56) References Cited

U.S. PATENT DOCUMENTS 5,271,737 A 12/1993 Baldwin et al.
5,800,551 A 9/1998 Williamson et al.
(Continued)

FOREIGN PATENT DOCUMENTS

EP 2965720 A1 1/2016
FR 3023471 A1 1/2016

OTHER PUBLICATIONS

Comprehensive Nano Stemless Shoulder Anatomic and Reverse, Surgical Technique, Biomet Orthopedics, 60 pages, 2012.
(Continued)

*Primary Examiner* — Jerrah Edwards
*Assistant Examiner* — Christine L Nelson
(74) *Attorney, Agent, or Firm* — SLEMAN & LUND LLP

(57) ABSTRACT

A stemless prosthetic shoulder joint may include a prosthetic humeral head and a stemless base. The stemless base may include a collar and an anchor extending from the collar intended to anchor the base into the proximal humerus. The anchor may include various features to enhance the fixation of the base, including hooks, threads, and/or expandable members that may be transitioned from a contracted insertion condition to an expanded implanted condition once the base is positioned in the bone. The anchor and/or collar may also include additional features to enhance fixation, such as geometries and surface features to enhance fixation to bone. The anchor may include a plurality of chisel slots to facilitate removal of bone during a revision surgery.

15 Claims, 26 Drawing Sheets

Related U.S. Application Data

No. 15/926,218, filed on Mar. 20, 2018, now Pat. No. 11,076,962.

(60) Provisional application No. 62/542,396, filed on Aug. 8, 2017, provisional application No. 62/474,800, filed on Mar. 22, 2017.

(52) U.S. Cl.
CPC .......... *A61F 2/4612* (2013.01); *A61F 2/4637* (2013.01); *A61F 2002/3082* (2013.01); *A61F 2002/3085* (2013.01); *A61F 2002/3092* (2013.01); *A61F 2002/30199* (2013.01); *A61F 2002/30205* (2013.01); *A61F 2002/30235* (2013.01); *A61F 2002/30332* (2013.01); *A61F 2002/30433* (2013.01); *A61F 2002/30477* (2013.01); *A61F 2002/30507* (2013.01); *A61F 2002/30571* (2013.01); *A61F 2002/30578* (2013.01); *A61F 2002/30579* (2013.01); *A61F 2002/30594* (2013.01); *A61F 2002/30779* (2013.01); *A61F 2002/30822* (2013.01); *A61F 2002/30841* (2013.01); *A61F 2002/30845* (2013.01); *A61F 2002/30881* (2013.01); *A61F 2002/30884* (2013.01); *A61F 2002/4007* (2013.01); *A61F 2002/4018* (2013.01); *A61F 2002/4037* (2013.01); *A61F 2002/4619* (2013.01)

(56) References Cited

U.S. PATENT DOCUMENTS

| | | | |
|---|---|---|---|
| 6,679,916 B1 | 1/2004 | Frankle et al. |
| 6,783,549 B1 | 8/2004 | Stone et al. |
| 6,953,478 B2 | 10/2005 | Bouttens et al. |
| 7,169,184 B2 | 1/2007 | Dalla Pria |
| 8,317,871 B2 | 11/2012 | Stone et al. |
| 8,425,614 B2 | 4/2013 | Winslow et al. |
| 8,506,638 B2 | 8/2013 | Vanasse et al. |
| 8,512,410 B2 | 8/2013 | Metcalfe et al. |
| 8,690,952 B2 | 4/2014 | Dallmann |
| 8,690,958 B2 | 4/2014 | Klawitter et al. |
| 8,753,402 B2 | 6/2014 | Winslow et al. |
| 8,840,671 B2 | 9/2014 | Ambacher |
| 8,845,742 B2 | 9/2014 | Kusogullari et al. |
| 8,876,908 B2 | 11/2014 | Katrana et al. |
| 8,992,623 B2 | 3/2015 | Hopkins et al. |
| 9,161,843 B2 | 10/2015 | Deffenbaugh et al. |
| D745,678 S | 12/2015 | Courtney et al. |
| 9,320,619 B2 | 4/2016 | Anthony et al. |
| 9,326,865 B2 | 5/2016 | Katrana et al. |
| 9,364,334 B2 | 6/2016 | Katrana et al. |
| 9,510,951 B2 | 12/2016 | Bachmaier |
| 9,585,769 B2 | 3/2017 | Lubensky et al. |
| 9,636,237 B2 | 3/2017 | Lubensky et al. |
| 9,693,880 B2 | 6/2017 | Olson et al. |
| 9,700,436 B2 | 6/2017 | Olson et al. |
| 9,700,437 B2 | 7/2017 | Anthony et al. |
| 9,713,540 B2 | 7/2017 | Anthony et al. |
| 9,820,859 B2 | 11/2017 | Gervasi et al. |
| 10,064,734 B2 | 9/2018 | Burkhead, Jr. et al. |
| 10,213,243 B2 | 2/2019 | Courtney, Jr. et al. |
| 2003/0187510 A1 | 10/2003 | Hyde |
| 2003/0236572 A1 | 12/2003 | Bertram |
| 2005/0278030 A1 | 12/2005 | Tornier et al. |
| 2007/0142917 A1 | 6/2007 | Roche et al. |
| 2007/0219638 A1 | 9/2007 | Jones et al. |
| 2009/0149961 A1 | 6/2009 | Dallmann |
| 2009/0164021 A1 | 6/2009 | Dallmann |
| 2009/0265011 A1 | 10/2009 | Mandell |
| 2009/0281630 A1 | 11/2009 | Delince et al. |
| 2011/0224673 A1 | 9/2011 | Smith |
| 2012/0109321 A1 | 5/2012 | Stone et al. |
| 2012/0296436 A1 | 11/2012 | Klawitter et al. |
| 2013/0018476 A1 | 1/2013 | Katrana et al. |
| 2013/0261629 A1 | 10/2013 | Anthony et al. |
| 2014/0005789 A1 | 1/2014 | Chavarria et al. |
| 2014/0025173 A1 | 1/2014 | Cardon et al. |
| 2014/0188231 A1 | 7/2014 | Poncet et al. |
| 2014/0296988 A1 | 10/2014 | Winslow et al. |
| 2014/0379089 A1 | 12/2014 | Bachmaier |
| 2016/0030197 A1 | 2/2016 | Anthony et al. |
| 2016/0038310 A1 | 2/2016 | Anthony et al. |
| 2016/0051367 A1 | 2/2016 | Gervasi et al. |
| 2016/0228264 A1 | 8/2016 | Anthony et al. |
| 2016/0324648 A1* | 11/2016 | Hodorek ............... A61F 2/4059 |
| 2017/0100251 A1 | 4/2017 | Ek et al. |
| 2017/0172763 A1 | 6/2017 | Lubensky et al. |
| 2017/0273800 A1 | 9/2017 | Emerick et al. |
| 2017/0340449 A1 | 11/2017 | Deransart et al. |
| 2018/0271668 A1 | 9/2018 | Kemp et al. |
| 2019/0192305 A1 | 6/2019 | Frankle et al. |

OTHER PUBLICATIONS

Extended European Search Report for Application No. 19207145.4, dated Feb. 18, 2020, pp. 1-4.

Extended European Search Report for EP Application No. 18163008, dated Jul. 12, 2018.

* cited by examiner

STEMLESS METAPHYSEAL HUMERAL IMPLANT

CROSS-REFERENCE TO RELATED APPLICATIONS

This present application is a continuation of U.S. patent application Ser. No. 17/372,600, filed Jul. 12, 2021, which is a continuation of U.S. Pat. No. 11,076,962, filed Mar. 20, 2018, which claims the benefit of the filing date of U.S. Provisional Patent Application No. 62/474,800, filed Mar. 22, 2017, and U.S. Provisional Patent Application No. 62/542,396, filed Aug. 8, 2017, the disclosures of which are hereby incorporated herein by reference as if fully set forth herein.

FIELD OF THE DISCLOSURE

The present application relates to a shoulder prosthesis, and in particular to a humerus implant.

BACKGROUND OF THE DISCLOSURE

Over time and through repeated use, bones and joints can become damaged or worn. For example, repetitive strain on bones and joints (e.g., through athletic activity), traumatic events, and certain diseases (e.g., arthritis) can cause cartilage in joint areas, for example, which normally provides a cushioning effect, to wear down. When the cartilage wears down, fluid can accumulate in the joint areas, resulting in pain, stiffness, and decreased mobility. The same can happen in cases where tendons in a joint become lax or soft tissues in or adjacent the joint become damaged or worn.

Arthroplasty procedures can be used to repair such damaged joints. During a typical arthroplasty procedure, an arthritic or otherwise dysfunctional joint can be remodeled or realigned. A prosthesis or prostheses can be implanted to repair the damaged region(s). Arthroplasty procedures may take place in any of a number of different regions of the body, such as the knees, hips, shoulders, or elbows, for example. One type of arthroplasty procedure is a shoulder arthroplasty, in which a damaged shoulder joint may be replaced with prosthetic implants. The shoulder joint may have been damaged by, for example, arthritis (e.g., severe osteoarthritis or degenerative arthritis), trauma, or a rare destructive joint disease.

Prostheses that are implanted into a damaged region may provide support and structure to the damaged region, and may help to restore the damaged region, thereby enhancing its functionality. Prior to implantation of a prosthesis in a damaged region, the damaged region may be prepared to receive the prosthesis. In the case of a shoulder arthroplasty procedure, one or more of the bones in the shoulder area, such as the humerus and/or glenoid, may be treated (e.g., cut, drilled, reamed, and/or resurfaced) to provide one or more surfaces that can align with the implant and thereby accommodate the implant.

It is often preferable to maintain as much of a patient's natural bone stock as possible during such a procedure. Prostheses generally have a certain life expectancy and in certain cases need to be replaced at some point. If one or more prostheses need to be removed and/or replaced in a revision procedure, a large bone void could be left after their removal. In certain cases, this bone void is not ideal for receipt of revision components. Preserving natural bone stock may be desirable for the ability to even perform a revision procedure.

In total or partial arthroplasty surgery, stemmed prostheses are often used which generally include a long stem that passes through a center of a long bone, the stem helping to anchor the remaining components of the prosthesis. However, stemmed prostheses may result in a large amount of healthy bone being removed in order to accommodate the stem. In some cases, stemless prostheses may be used, which may result in less healthy bone stock being removed. However, in some cases stemless prostheses may not anchor the particular prosthesis as well as a stemmed prosthesis would. In additional, some stemless shoulder prostheses may require the removal of significant proximal humeral bone, which may compromise the proximal humerus bone and result in more challenging revision surgeries.

BRIEF SUMMARY OF THE DISCLOSURE

According to one aspect of the disclosure, a base member of a stemless shoulder implant includes a proximal collar and an anchor. The anchor extends distally from the collar along a longitudinal axis, the anchor extending from a first end coupled to the collar to a tip at a second end of the anchor and having an outer wall having a plurality of peaks and a plurality of troughs. Each trough is adjacent to at least one peak, and each peak extends farther radially outward of the longitudinal axis than an adjacent one of the troughs. Each peak is adapted to engage a bone. The outer wall includes a flexible portion and a static portion, the flexible portion having an expanded condition in which the flexible portion extends radially outwardly of adjacent surfaces of the static portion and a constrained condition in which the flexible portion is substantially flush with the adjacent surfaces of the static portion. The anchor may be tapered along the longitudinal axis. A recess may be adapted to receive an insertion or extraction instrument, wherein upon insertion of the instrument into the recess, the flexible portion transitions from the expanded condition to the constrained condition. The flexible portion may be adapted to transition from the constrained condition into the expanded condition upon removal of the instrument from the recess. Each peak may transition into a proximally adjacent trough at a proximally-facing hook. The flexible portion may be at least partially defined by a slot extending through the outer wall and may be adapted to allow for expansion of the flexible portion. The base may include four of the flexible portions and four corresponding slots positioned at substantially equal intervals around a circumference of the outer wall of the anchor.

According to another aspect of the disclosure, a base member of a stemless shoulder implant includes a proximal collar, a central anchor, and a plurality of peripheral anchors. The proximal collar has a proximal surface, a bone-engaging surface, and a plurality of holes extending from the proximal surface to the bone-engaging surface. The central anchor extends distally along a longitudinal axis of the base member from the bone-engaging surface of the collar a first distance to a central tip and having a plurality of flutes extending toward the tip. The plurality of peripheral anchors are each positioned radially outwardly of the central anchor and extend distally from the bone-engaging surface of the collar a second distance to a peripheral tip, the first distance being greater than the second distance. The proximal surface of the collar may include an opening adapted to mate with a prosthetic humeral head component. At least a portion of the central anchor may include a porous metal surface. The peripheral anchors may include flutes extending from the bone-engaging surface to the peripheral tip. A recessed groove may extend circumferentially around at least a portion of the central anchor at the connection of the bone-engaging surface and the central anchor. Each flute on the central anchor may include two edges extending from the proximal collar to the central tip, each edge having an apex extending a greater radial distance from the longitudinal axis than any other portion of the edge. Each flute on the central anchor may include an enhanced fixation surface extending from the recessed groove to a point circumferentially aligned with the adjacent apices, the enhanced surface including a porous metal surface. At least one of the plurality of holes may be positioned adjacent the enhanced fixation surface on one of the flutes. At least one of the plurality of holes may be oblong with a major axis extending radially outwardly from the longitudinal axis. The at least one hole may be positioned adjacent one of the peripheral anchors. The plurality of peripheral anchors may include four peripheral anchors positioned at substantially equal circumferential intervals around the collar.

According to still another aspect of the disclosure, a base member of a stemless shoulder implant includes an annular proximal collar, a threaded anchor, and a socket. The collar has a proximal surface, a bone-engaging surface, and defines an open interior space. The anchor extends distally from the bone-engaging surface of the collar. The socket is positioned within the open interior space of the collar and defines an opening extending from the proximal surface of the collar to a distal end of the anchor.

According to yet another aspect of the disclosure, a base member of a stemless shoulder implant includes a proximal collar, an anchor, and a rotatable nut. The collar has a proximal surface, a bone-engaging surface, and a central opening extending along a longitudinal axis of the base member from the proximal surface to the bone-engaging surface. The anchor extends distally from the bone-engaging surface of the collar to a free end, the anchor having a plurality of flanges extending from the bone-engaging surface to the free end. Each flange has an inner surface with first threads and a distal tapered portion. The nut has an outer diameter and second threads adapted to engage the first threads of the flanges. The base member has a constrained condition in which the nut is positioned proximal to the distal tapered portions of the flanges and the distal tapered portions of the flanges define an internal diameter less than the outer diameter of the nut. The base member also has an expanded condition in which the nut is radially aligned with the distal tapered portions of the flanges. The base member transitions from the constrained condition to the expanded condition upon rotation of the nut, and rotation of the nut causes the nut to translate distally with respect to the inner surfaces of the flanges. A support member may extend distally from the bone-engaging surface to a distal surface of the support. When the nut is in contact with the distal surface of the support, the base member is in the constrained condition. The support member may include a central opening contiguous with the central opening of the collar.

According to still another aspect of the invention, a base member system of a stemless shoulder implant includes a proximal collar, a central anchor, and a plurality of screws. The proximal collar has a proximal surface, a bone-engaging surface, and a plurality of holes extending from the proximal surface to the bone-engaging surface. The central anchor extends distally along a longitudinal axis of the base member from the bone-engaging surface of the collar a first distance to a central tip. The plurality of screws are adapted to be received in the plurality of holes, at least one of the plurality of screws having a different length than another of the plurality of screws.

In yet another aspect of the present disclosure, a base member of a stemless shoulder implant includes a proximal collar that has a proximal surface and a bone-engaging surface opposite the proximal surface, a central anchor that extends distally along a longitudinal axis of the base member from the bone-engaging surface of the collar a first distance to a central tip. The central anchor has a plurality of ribs that extend toward the central tip. The base member includes at least one chisel slot extending from the bone-engaging surface to the proximal surface adjacent a portion of the central anchor. The chisel slot is configured to receive a tool for removing bone.

In other embodiments, the collar of the base member may define a first hole and a second hole, both holes extending from the proximal surface to the bone-engaging surface. The first hole may have a first diameter and the second hole may have a second diameter, the second diameter being greater than the first diameter. The first hole may be configured to receive a variable angle screw, and the second hole may be configured to receive a fixed angle screw. The first hole may be positioned superior to the second hole when implanted. The plurality of ribs may include four ribs positioned in a substantially "X"-shaped configuration. A first rib may be positioned about 60 degrees from a second rib and about 120 degrees from a third rib, the third rib may be positioned about 60 degrees from a fourth rib, and the second rib may be positioned about 120 degrees from the fourth rib. The chisel slot may have a substantially "M"-shaped configuration. The first hole may be positioned between the first and second ribs and the second hole may be positioned between the third and fourth holes. At least one peripheral anchor may be positioned radially outward of the chisel slot. In other embodiments, the base member may form a system with a chisel tool. The chisel tool may have a shaft extending along a longitudinal axis and a cutting structure connected to a distal end of the shaft, the cutting structure may be sized and configured to fit within at least a portion of the chisel slot of the base. The cutting structure may have a substantially "M"-shaped configuration. The cutting structure may have a distal surface having a plurality of teeth adapted to cut bone. The cutting structure may have side walls having teeth adapted to cut bone.

In other embodiments, the base member may include a plurality of peripheral anchors each positioned radially outwardly of the central anchor and extending distally from the bone-engaging surface of the collar a second distance to a peripheral tip, in which the first distance is greater than the second distance. The at least one chisel slot may be positioned between a first peripheral anchor and the central anchor. The plurality of ribs may include four ribs, each rib positioned at an angle of about ninety degrees relative to an adjacent rib. The four ribs together may define four quadrants of the collar. The at least one chisel slot may include four chisel slots, each of the four chisel slots being positioned in a corresponding one of the four quadrants of the collar. A first pair of ribs may be substantially parallel with each other and extend a first total distance across the collar, and a second pair of ribs may be substantially parallel with each other and extend a second total distance across the collar, the second total distance being greater than the first total distance. The first pair of ribs may be substantially perpendicular to the second pairs of ribs. The at least one chisel slot may be asymmetric about at least two planes. At least a portion of the central anchor may include a bone ingrowth coating. The coating may extend between about 40% and about 50% of the first distance of the central anchor. The chisel slot may be positioned along a path that tracks adjacent to a first rib and a second rib of the plurality of ribs, the first and second ribs being circumferentially adjacent one another. The first and second ribs may be substantially perpendicular to each other.

In still another aspect of the present disclosure, a base member of a stemless shoulder implant includes a proximal collar having a proximal surface and a bone-engaging surface opposite the proximal surface, a central anchor extending distally along a longitudinal axis of the base member from the bone-engaging surface to a distal tip. The central anchor includes a plurality of ribs. The base member includes at least one chisel slot extending from the bone-engaging surface to the proximal surface and extending between two adjacent ribs of the plurality of ribs. The base member may include a plurality of peripheral anchors each positioned radially outwardly of the central anchor and extending distally from the bone-engaging surface of the collar a second distance to a peripheral tip, the first distance being greater than the second distance. The plurality of ribs of the central anchor may include four ribs, each rib positioned at an angle of about ninety degrees relative to an adjacent rib, the four ribs together defining four quadrants of the collar. The at least one chisel slot may include four chisel slots, each of the four chisel slots being positioned in a corresponding one of the four quadrants of the collar. The at least one chisel slot may be asymmetric about at least two planes. Each rib may include outer surface having a width, the width decreasing in a proximal to distal direction.

DETAILED DESCRIPTION

It should be understood that although the term "stemless implant" is used herein, the term does not indicate that a stemless implant fully lacks any anchor, but rather a stemless implant may include an anchor that is significantly smaller and/or shorter than stems of typical known stemmed implants. Further, the stemless implants of the present disclosure generally include a base member intended for coupling to an end of a first bone of a joint, such as a humerus or femur, and an articulating member intended to attach to the base member and to provide articulation with the second bone of the joint (or a corresponding prosthesis attached to the second bone). Further, as used herein, the term "proximal" refers to a location closer to an individual's heart, and the term "distal" refers to a location farther away from the individual's heart. When used in the context of an implant, the terms "proximal" and "distal" refer to locations on the implant closer to, or farther away from, the heart when the implant is implanted in an intended manner.

Figure 1:
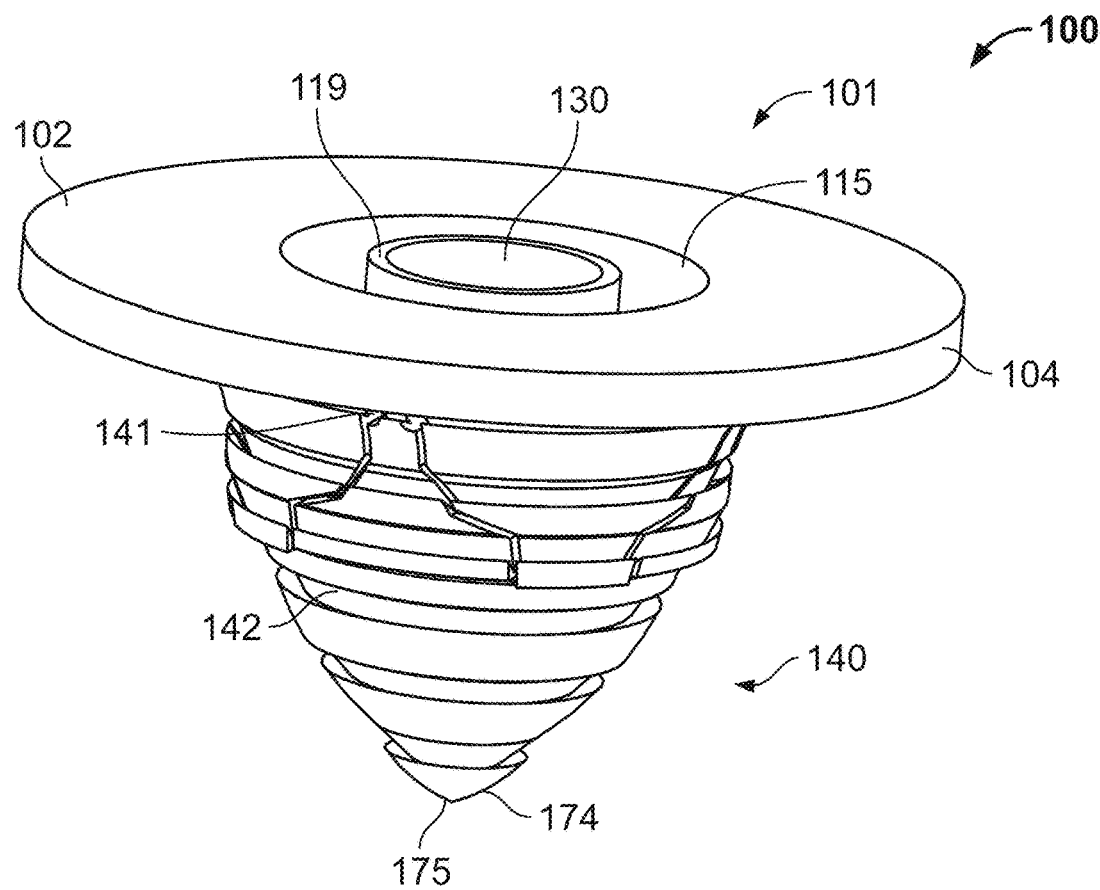
FIG. 1 is a top perspective view of a base of a shoulder implant according to a first aspect of the disclosure.
Figure 2:
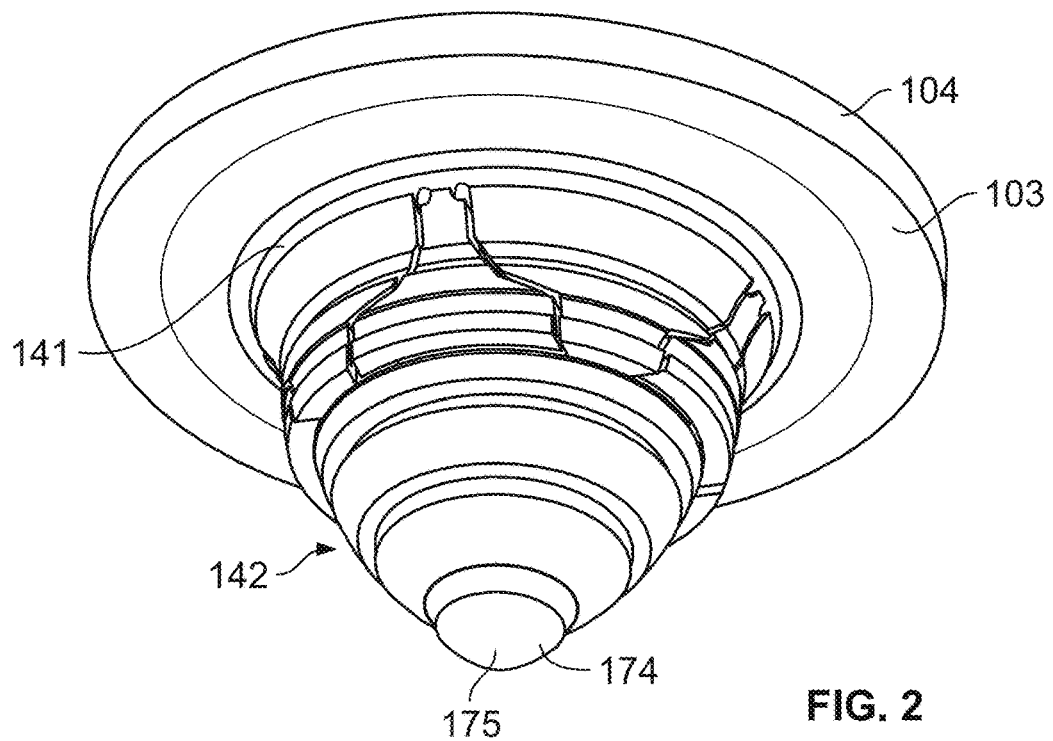
FIG. 2 is a bottom perspective view of the base of FIG. 1.

FIGS. 1 and 2 show a base 100 of a stemless implant according to a first aspect of the disclosure. Base 100 generally includes collar 101 and central anchor 140 coupled thereto. Collar 101 may be generally cylindrical or annular and includes a proximal end surface 102, a distal bone-engaging surface 103, and side flange surface 104 extending along the circumference of the collar. As shown in FIG. 1, proximal end surface 102 may be flat, but it can also be inclined or sloped in some embodiments. As in FIG. 1, side flange surface 104 may have a uniform height, measured from distal to proximal ends of side flange surface 104, or the height may be varied along proximal surface 102. Although shown as generally cylindrical or annular, collar 101 may have other shapes. Anchor 140 is coupled to collar 101 at a first end 141 and extends distally from the collar along a longitudinal axis 135 to a second end 174. In the illustrated embodiment, anchor 140 is tapered along longitudinal axis 135 so that first end 141 has a relatively large diameter, with the diameter of the anchor generally narrowing toward second end 174 until the anchor terminates in distal tip 175; however, in some situations it may be appropriate for anchor 140 to be of uniform size throughout and not tapered. Anchor 140 further includes outer wall 142 extending from first end 141 toward distal tip 175.

Figure 3:
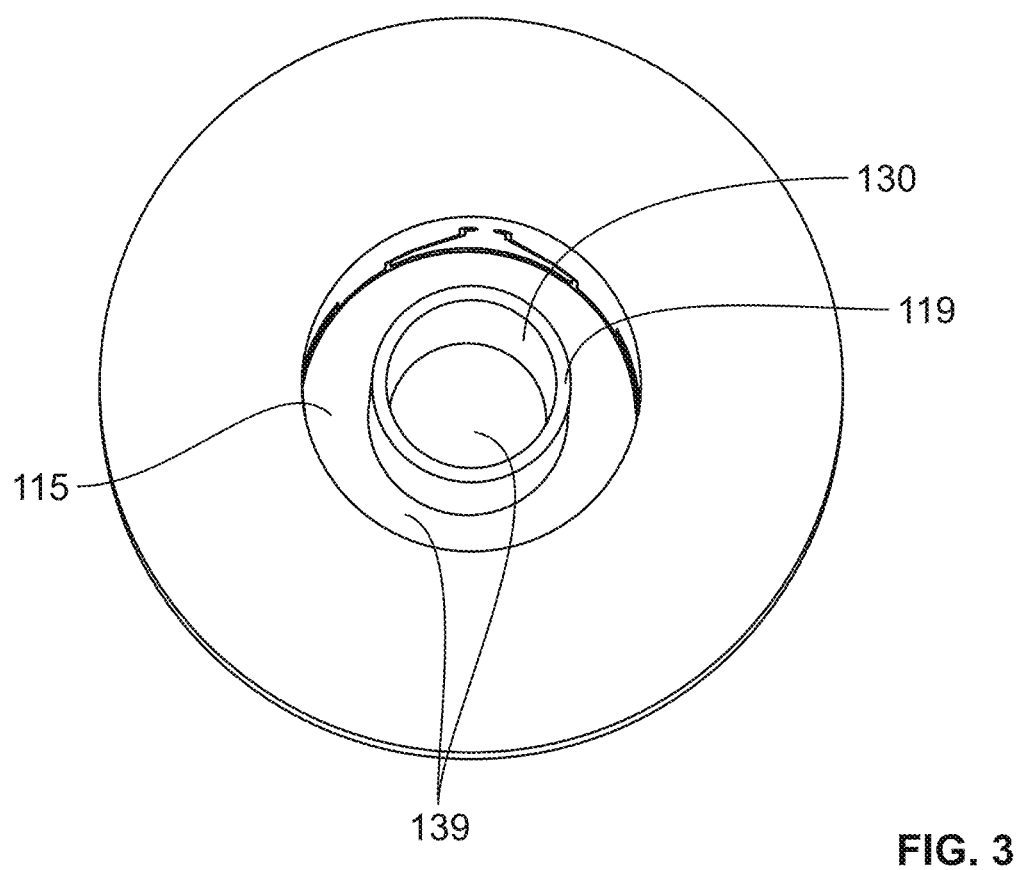
FIG. 3 is a top view of the base of FIG. 1.

As shown in FIGS. 1 and 3, base 100 includes an annular rim 119 positioned within an interior cavity of collar 101. Rim 119 defines an opening 130 which is adapted to receive an articulating component (not shown) of the stemless implant. In the illustrated example, base 100 may be adapted to couple to a proximal humerus of a patient, with a prosthetic humeral head adapted to couple to the base via opening 130, the prosthetic humeral head intended to articulate with a native or prosthetic glenoid of the shoulder joint. Although rim 119 and opening 130 may have any shape that suitably mates with the corresponding portion of the prosthetic humeral head, in one example a taper such as a Morse taper may be used to lock the prosthetic humeral head to rim 119. The proximal end of rim 119 may be substantially flush with the proximal surface 102 of collar 101, although in some embodiments it may extend either proximally or distally of proximal surface 102. In the illustrated embodiment, the opening 130 defined by rim 119 extends from proximal end surface 102 of collar 101 along longitudinal axis 135 to a proximal surface 139 of anchor 140. From surface 139 to tip 175, anchor 140 may be generally solid, with the exceptions noted below in connection with the flexible portions of outer wall 142.

The space between the inner circumference of collar 101 and the outer circumference of rim 119 defines a circular or cylindrical recess 115. Recess 115 extends from proximal surface 102 distally along longitudinal axis 135 to surface 139. Rim 119 separates opening 130 and recess 115. Prior to attaching a prosthetic humeral head to base 100, or after removing a prosthetic humeral head from the base, tools such as insertion and extraction tools may be inserted into opening 130 and/or recess 115, as discussed below.

Figure 4:
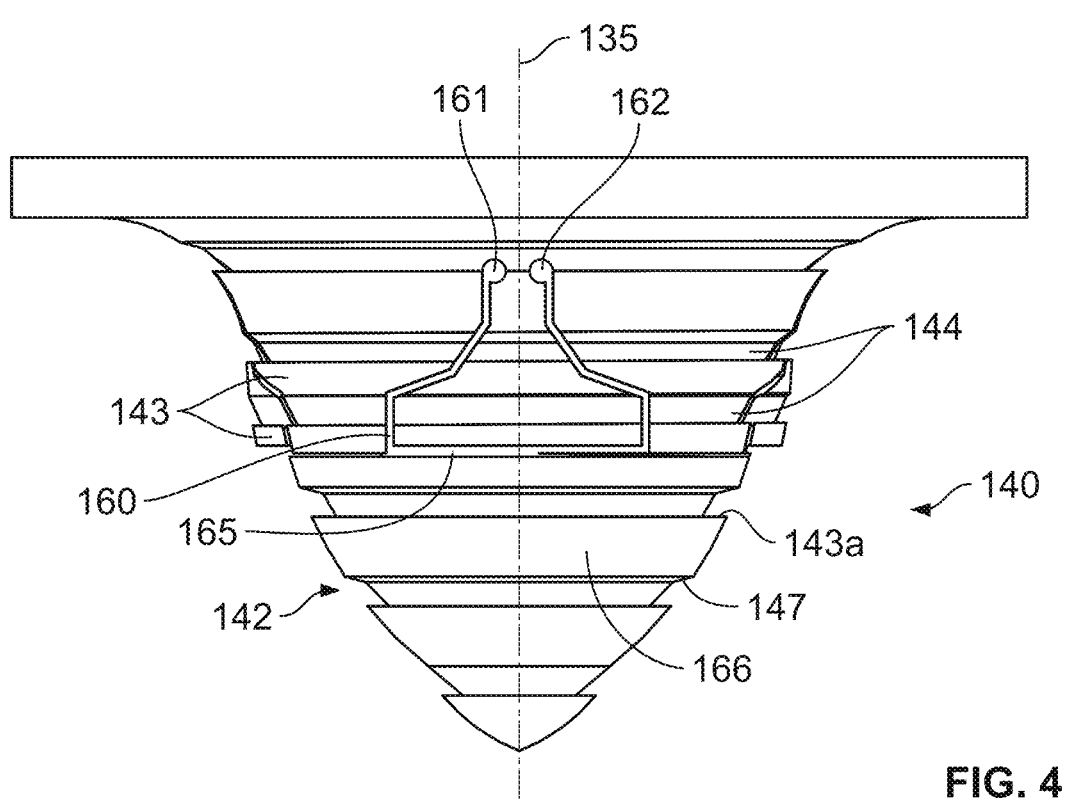
FIG. 4 is a side view of the base of FIG. 1.

FIG. 4 shows a side view of base 100, including outer wall 142 of anchor 140. As can be seen more clearly in FIG. 4, outer wall 142 may have a serrated configuration in which the outer wall includes alternating peaks 143 and troughs 144 in the proximal-to-distal direction, with each peak transitioning into a trough and each trough transitioning into a peak. As shown in FIG. 4, peaks 143 and troughs 144 may be disposed substantially circularly around outer wall 142, with the outer surfaces of the peaks and the troughs together defining the outer wall. In other embodiments, peaks 143 and troughs 144 may be disposed helically around outer wall 142 in a screw-like configuration. As noted above, each trough 144 is positioned adjacent to at least one peak 143, and preferably two peaks. Each peak 143 may extend farther radially outward from the longitudinal axis 135 than each adjacent trough 144. The transition between the outer circumference of each peak 143 to a distally adjacent trough 143 forms a distal surface 147 that is shaped frustoconically.

Although the outer circumferential surface of each peak 143 may be angled along the general contour of anchor 140, each peak may also include a generally curved surface, where a peak transitions into an adjacent trough 144. With this configuration, the proximal surface of each peak forms a counter support to resist pull-out, torque out, and/or lever out of the base 100 after implantation. For example, in the illustrated embodiment, the transition between the outer circumference of each peak 143 to a proximally adjacent trough 144 forms a hook 143a. Hook 143a may extend radially outwardly from adjacent troughs 144 in a proximal-facing hook shape. Hooks 143a can be advanced into the native bone to fix the anchor to the bone. Once hooks 143a are engaged in the bone, motion is restricted due to the hooked shape of hooks 143a.

Figure 5:
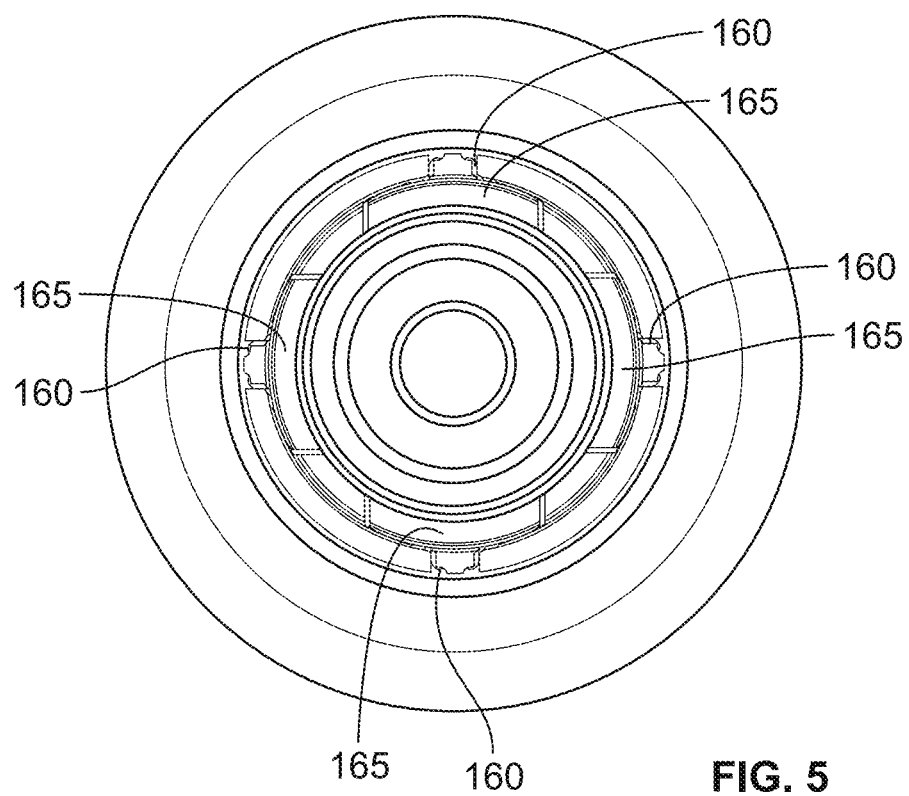
FIG. 5 is a bottom view of the base of FIG. 1.

FIG. 4 further illustrates a plurality of slots 160 formed in the outer wall 142 of anchor 140. Slots 160 are designed to enable flexible portions 165 of outer wall 142 to flex and extend radially outwardly of static portions 166. Each slot 160 may extend through outer wall 142 so that the slot fully extends from the outer surface of the anchor and into recess 115. Although various methods may be used to create slots 160, in the illustrated embodiment the slot extends from holes 161 and 162 distally to a bottom surface 165 of the slot. Bottom surface 165 may extend around a portion of a circumference of anchor 140 and may be positioned in a plane that is parallel to proximal surface 102 of collar 101 and is coextensive with a plane defined by surface 139. Holes 161 and 162 may be positioned on proximal portions of outer wall 142 near first end 141. Holes 161 and 162 may be adjacent to each other but do not overlap, such that a thin connection is maintained between flexible portion 165 and the remainder of outer wall 142. Although the bottom surface 165 of slot 160 is shown as being disposed through outer wall 142 at an angle generally perpendicular to longitudinal axis 135, the angle may be of varying degrees. As shown in FIG. 5, base 100 may include four slots 160 that form four flexible portions 165 positioned at substantially equal intervals around the circumference of anchor 140, but it should be understood that more or fewer slots and/or flexible portions may be provided as desired.

Each flexible portion 165, which may be thought of as the portions of outer wall 142 within a particular slot 160, may be biased outwardly from adjacent surfaces of static portion 166 so that, in the absence of applied force, portions of each flexible member extend farther radially outward from longitudinal axis 135 compared to circumferentially adjacent areas of static portion 166. With this configuration, a tool may be used to pull the flexible portions 165 radially inward to generally align with static portion 166 upon either insertion of base 100 into bone, or extraction of the base out of bone, such that the outer wall 142 of anchor 140 forms a substantially smooth surface. For example, an insertion and/or extraction tool (not shown) may be inserted into opening 130 and/or recess 115 to engage each flexible portion 165 to pull the flexible portions radially inward. This constrained or contracted condition may be referred to as the insertion and/or removal condition. During implantation of base 100, for example into cancellous bone in a prepared proximal humerus, anchor 140 may be driven into the cancellous bone until collar 101 is substantially flush with the proximal humerus. Using a tool to transition base 100 to the insertion condition prior to implantation may provide a substantially smooth surface of the outer wall 142 of anchor 140 to ease the insertion of the base into the bone. Once base 100 is in the desired position in the proximal humerus, the tool may be disengaged from base 100, allowing flexible portions 165 to flex radially outwardly into the bone in which the base is implanted. This condition may be referred to as the implanted or expanded condition. This additional radial force may further aid in achieving suitable fixation of the base 100, despite the base being stemless. Further, during a revision procedure in which base 100 must be removed from the bone, merely pulling the base proximally out of the bone risks trauma due to the flexible portions 165. Thus, a tool similar or identical to that described above may again be inserted into opening 130 and/or recess 115 and engage each of the flexible portions 165 to move them radially inwardly into the removal condition. This transition helps to create clearance between the proximal humerus and the outer wall 142 of anchor 140, particularly at the locations of the flexible portions 165. In some embodiments, in the absence of applied force, the flexible portions 165 may extend less than about 2 mm or about 3 mm compared to circumferentially aligned areas of static portion 166. Although this amount of extension may seem small, the radial extension may enable the hooks 143a associated with the flexible portions 165 to further engage the bone for increased fixation. It should also be understood that the tool used to transition the base from the insertion condition or removal condition to the implanted or expanded condition may be the same tool that is used to hold the base 100 during implantation or explantation, although it may also be a separate tool with no additional function.

Figure 6:
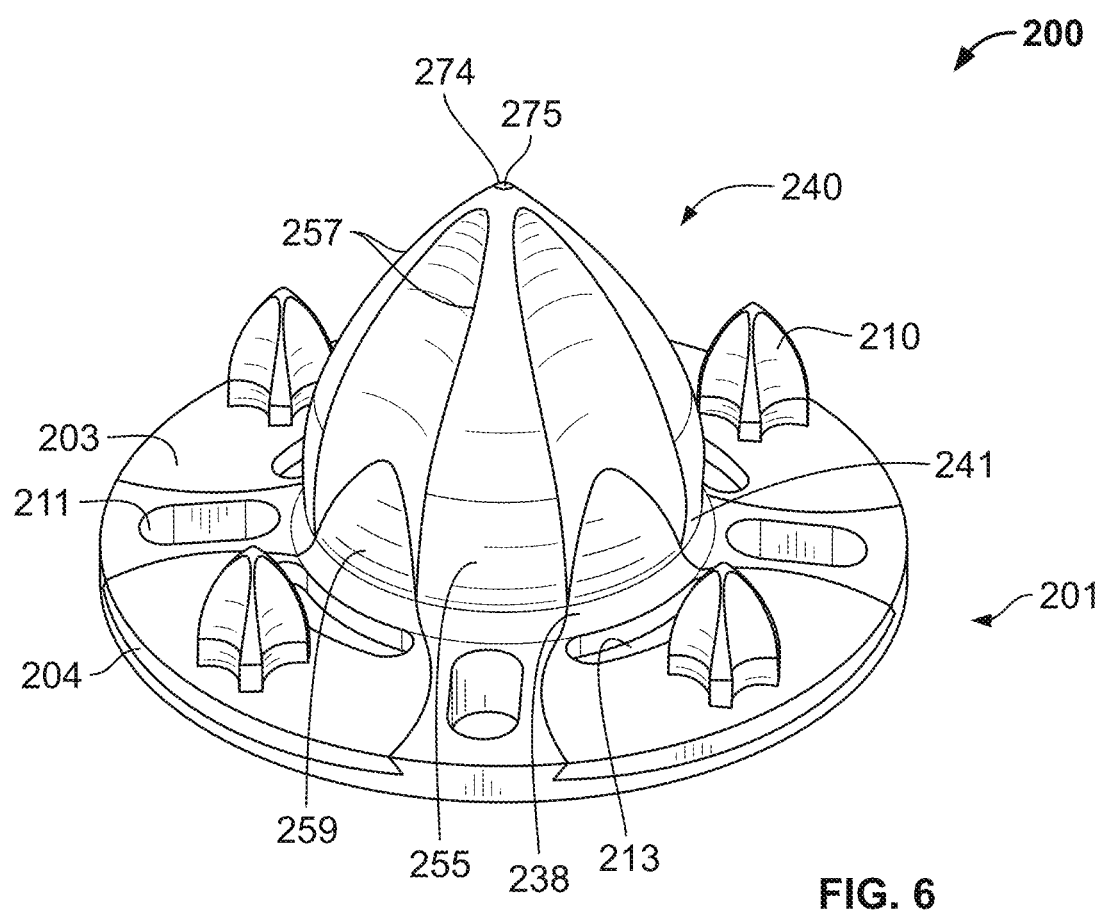
FIG. 6 is a side perspective view of a base of a shoulder implant according to a second aspect of the disclosure.
Figure 7:
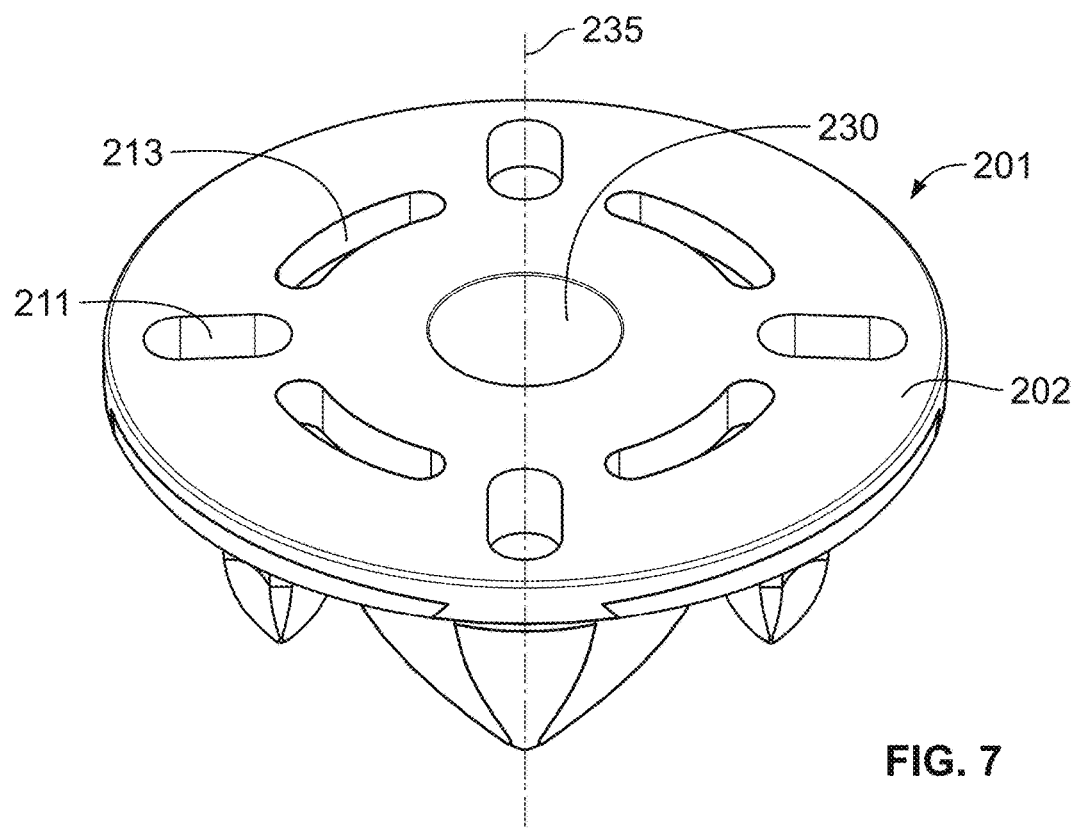
FIG. 7 is a top perspective view of the base of FIG. 6.

FIGS. 6 and 7 show a base 200 of a stemless implant according to a second embodiment of the disclosure. Base 200 generally includes collar 201 coupled with central anchor 240. Collar 201 may be generally cylindrical or annular and includes a proximal end surface 202, a distal bone engaging-surface 203, and a side flange surface 204. Proximal end surface 202 may be flat as shown, but in other embodiments it may be inclined or sloped. Side flange surface 204 may have a uniform height, the height measured from distal to proximal ends of side flange surface 204, or the height may vary along proximal end surface 202. Although shown as generally cylindrical or annular, collar 201 may have other shapes.

Base 200 includes central anchor 240 coupled to collar 201 at a first end 241 and extending distally from the collar along a longitudinal axis 235 to a second end 274. In the illustrated embodiment, anchor 240 is tapered along longitudinal axis 235 so that first end 241 has a relatively large diameter, with the diameter of the anchor generally narrowing toward second end 274 until the anchor terminates in distal tip 275; although, in some situations it may be appropriate for, anchor 240 to be of uniform size throughout and not tapered.

Figure 8:
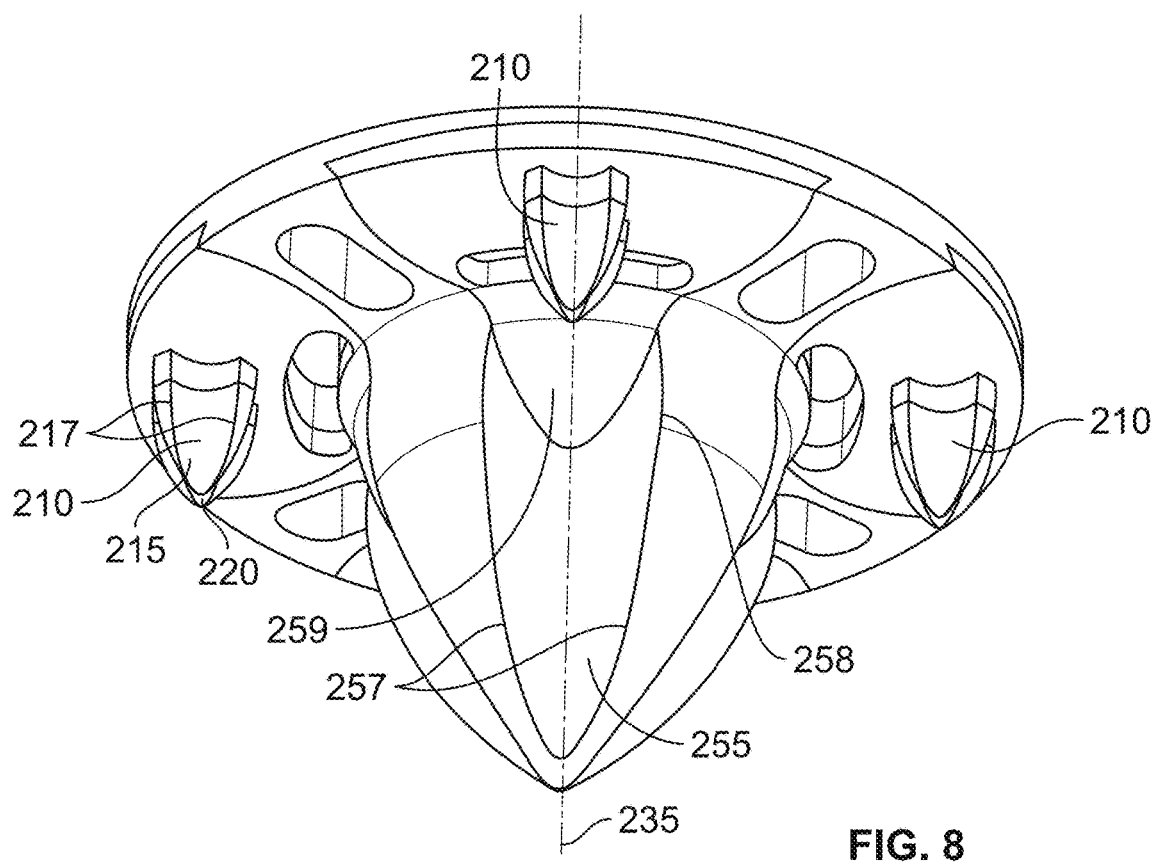
FIG. 8 is another side perspective view of the base of FIG. 6.

When used as part of a shoulder implant system, anchor 240 may be configured to be driven into the metaphyseal cancellous bone of the humerus and to facilitate engagement between base 200 and the bone for fixation. Anchor 240 may include a plurality of flutes 255 which may extend part or all of the longitudinal length of the anchor, for example from bone-engaging surface 203 to distal tip 275. Each flute 255 may be positioned between two edges 257, with the flute being recessed radially inwardly toward longitudinal axis 235 compared to the edges. Edges 257 may extend radially outwardly from longitudinal axis 235 to varying degrees depending on the position along the longitudinal axis. For example, edges 257 may have a minimum amount of radial extension from longitudinal axis 235 at or near distal tip 275. The distance which the edges 257 extend radially outwardly from longitudinal axis 235 may then increase gradually in the proximal direction toward bone-engaging surface 203. The edges 257 may reach their greatest amount of outward radial extension from longitudinal axis 235 at apex 258. From apex 258 to bone-engaging surface 203, the distance which edges 257 extend radially outward from longitudinal axis 235 may decrease until the edges connect to bone-engaging surface 203. Flutes 255 are preferably concave between two adjacent edges 257. Each flute 255 may include an enhanced fixation surface 259 in the region between bone-engaging surface 203 and a portion of the flute circumferentially aligned with apex 258. The enhanced fixation surface 259 may take the form of a porous metal surface, such as porous titanium alloy, including Tritanium® by Howmedica Osteonics Corporation. As shown in FIG. 8, fixation surface 259 may be in the general shape of a trough and may be convex. Fixation surfaces 259 may provide for enhanced in-growth of bone into anchor 240, facilitating better fixation of base 200 following implantation. Fixation surfaces 259 may be rougher than the adjacent surfaces of anchor 240, resulting in greater friction between the fixation surface 259 and the bone. This increased friction may help provide additional fixation by providing additional resistance against pull-out forces.

A fixation ring 238 may surround central anchor 240, the fixation ring extending circumferentially around the central anchor at its connection with bone-engaging surface 203. Fixation ring 238 may generally take the form of a recessed groove. As explained in greater detail below, upon implantation of base 200 into cancellous bone, the bone may flow into fixation ring 238 to help provide additional fixation. As shown in FIG. 7, fixation surfaces 259 may extend into portions of fixation ring 238 to provide stronger fixation to the bone.

When implanting base 200 into a bone, such as the cancellous bone at the proximal end of the humerus, distal tip 275 of anchor 240 is driven into the bone. Because cancellous bone is relatively soft, the bone may effectively flow along anchor 240, and in particular along the flutes 255 of the anchor. After the apex 258 of the edges 257 passes into the bone, some volume of bone may effectively "spring" back into the areas of flute 255 adjacent enhanced fixation surfaces 259 and also into fixation ring 238. The positioning of the fixation ring 238 in the area of the flutes 255 proximal to the apex 258 results in stronger pull-out resistance for base 200, with the resistance increasing further as bone grows into the pores of fixation surface 259 and fixation ring 238.

Figure 9:
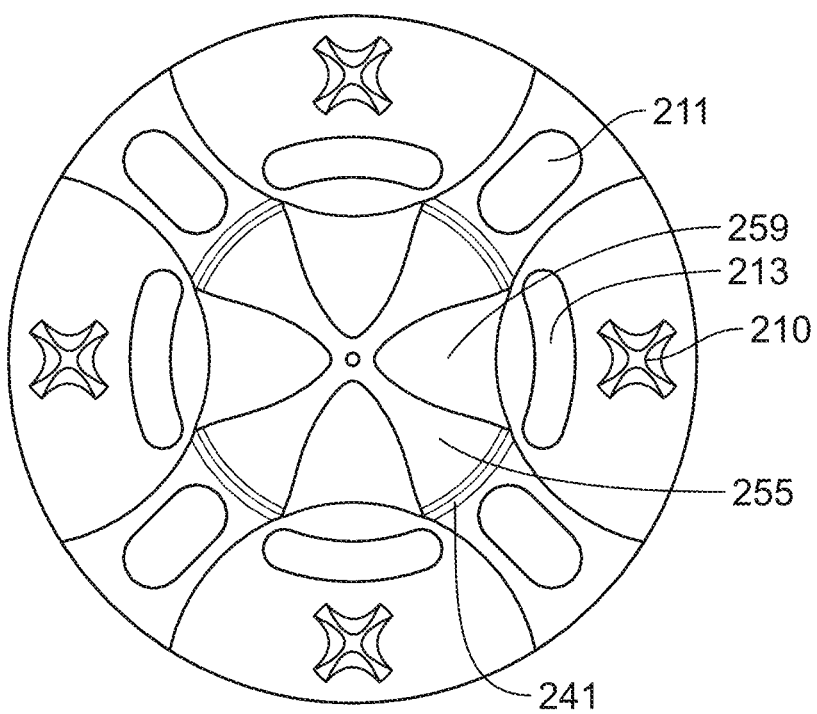
FIG. 9 is a bottom view of the base of FIG. 6.

As shown in FIGS. 8 and 9, collar 201 defines a plurality of holes 211 and 213 extending from proximal end surface 202 to bone-engaging surface 203 and includes a plurality of peripheral anchors or pegs 210 extending distally from bone-engaging surface 203 to distal tips 220. Pegs 210 aid in the fixation of base 200 to the bone, and may particularly assist in initial fixation. While there can be any number of pegs 210 on collar 201, preferably there are four pegs positioned at substantially equal circumferential intervals around the collar. As shown best in FIG. 9, pegs 210 may be located radially outward of holes 213, although other relative spacing between pegs 210 and holes 213 may be appropriate. The use of at least four pegs 210 may provide for enhanced feedback, especially compared to the use of three or fewer pegs, while seating base 200 into the prepared bone during insertion. For example, upon initial contact of pegs 210 with a prepared flat bone surface, the surgeon may be able to easily determine if each of the pegs is simultaneously in contact with the bone. In particular, if all four pegs 210 are in contact with the proximal surface of the bone, the base 200 should not experience any significant amount of rocking or tilting. If the surgeon notices rocking of the base 200, it should be clear that all four pegs 210 are not simultaneously in contact with the bone. If base 200 included three pegs, on the other hand, this rocking motion would not be expected despite a mismatch between a plane defined by the tips of the pegs and a plane of the prepared proximal bone.

As shown in FIG. 8, pegs 210 extend distally from bone-engaging surface 203 to distal tips 220. Pegs 210 may also include flutes 215. Each flute 215 is positioned between two edges 217, and flutes 215 may be generally concave between the two edges 217. Each peg 210 may have a substantially identical structure to central anchor 240 but scaled to a smaller size. Those structures may provide substantially the same effect as the corresponding features on central anchor 240, although the effects may be less dramatic due to the smaller sizes of the pegs compared to the central anchor. However, in other embodiments, the pegs 210 do not need to have identical but scaled down features as the central anchor 240.

As shown in FIGS. 7-9, holes 211 and 213 extend from proximal surface 202 to bone-engaging surface 203. Holes 211 and 213 may be in any shape, round, oval, oblong, etc. Alternatively, holes 211 may be openings extending from proximal surface 202 to bone-engaging surface 203 near side wall 204, such that side wall 204 includes curved recesses in the side wall. In the illustrated embodiment, holes 211 are oblong and a major axis of each hole extends from a point near central anchor 240 radially outwardly toward a point near side flange 204 of collar 201. Holes 213, may also be oblong, and slightly curved so that a major axis of each hole extends in the circumferential direction around central anchor 240. Holes 211 and 213 may have various uses. For example, holes 211 and 213 may be used for passing one or more sutures through to aid in fixation of an object to the base 200. Still further, holes 211 and 213 may be used to engage insertion and/or extraction instrumentation. In the illustrated embodiment, there are four holes 211 and four holes 213, but there may be more or fewer of each of hole 211 and 213. Further, there is no requirement that the number of holes 211 equal the number of holes 213.

In addition to the uses described above, holes 213 may be sized and positioned to facilitate a revision procedure after the base 200 has been implanted into a patient for an amount of time. In the embodiment illustrated in FIG. 8, holes 213 are positioned adjacent fixation surfaces 259 of flutes 255 and fixation ring 238. With this positioning of holes 213, a surgeon may insert a tool through holes 213 in order to chisel, ream, or otherwise cut away at bone that is adjacent to fixation surface 259 and/or fixation ring 238. Strategically cutting away these areas of bone allows for easier removal of base 200 so that a new device may be implanted in its place.

Each hole 211 may be spaced generally midway between two adjacent pegs 210. However, in some embodiments each hole 211 may be positioned adjacent a corresponding peg 210. In such an embodiment, each hole 211 is preferably disposed adjacent a same side of the associated peg 210. In other words, each hole 211 may be disposed on the right side adjacent to each peg 210, or each hole 211 may be disposed on the left side adjacent to each peg. With each hole 211 adjacent the same side of an associated peg 210, a tool inserted through the holes 211 may be used to ream or cut bone adjacent pegs 210, such that the base 200 may be rotated to move the pegs into the bone cavity adjacent the holes 211. This process may allow for easier removal of base 200 during a revision surgery. Rather than having one hole associated with each peg 210, each peg may include two holes on either side of the peg so that the base 200 may be rotated in either direction to facilitate extraction of the base.

As with base 100, base 200 may further define an opening 230. Opening 230 may extend distally along longitudinal axis 235 from proximal surface 202 of collar 201. Opening 230 may extend partially or fully through anchor 240 along longitudinal axis 235 or it may be shallow and extend only into collar 201. A humeral head component (not shown) may be placed within opening 230 and attached thereto, for example by a taper lock such as a Morse taper. The humeral head component may be attached by any known securement means including screw or friction fit.

It should be understood that bases 100 and 200 may be formed of any suitable prosthetic grade material, including, for example, titanium alloys and/or other biocompatible metals and metal alloys. In some embodiments of base 200, the porous portions of the base, such as fixation surface 259 and fixation ring 238, may be provided via additive manufacturing over a base material such as titanium alloy. Further, although holes 211 and 213 are only described in connection with base 200, similar or identical holes may be provided in base 100. Still further, base 100 may include surfaces similar to fixation surfaces 259 and fixation ring 238, for substantially the same purpose of increased fixation.

FIGS. 10-13 show base 300 of a stemless implant according to another aspect of the disclosure. Base 300 generally includes collar 301 coupled with central anchor 340. Collar 301 may be generally cylindrical or annular and includes a proximal end surface 302, a distal bone engaging-surface 303, and a side flange surface 304. Proximal end surface 302 may be flat as shown, but in other embodiments it may be inclined or sloped. Side flange surface 304 may have a uniform height, the height measured from distal to proximal ends of side flange surface 304, or the height may vary along proximal end surface 302. Although shown as generally cylindrical or annular, collar 301 may have other shapes.

Base 300 includes central anchor 340 coupled to collar 301 at a first end 341 and extending distally from the collar along a longitudinal axis 335 to a second end 374. In the illustrated embodiment, anchor 340 is slightly tapered along longitudinal axis 335 so that first end 341 has a relatively larger diameter, with the diameter of the anchor slightly narrowing toward second end 374; although, in some embodiments, anchor 340 may be of uniform size and not tapered.

Figure 10:
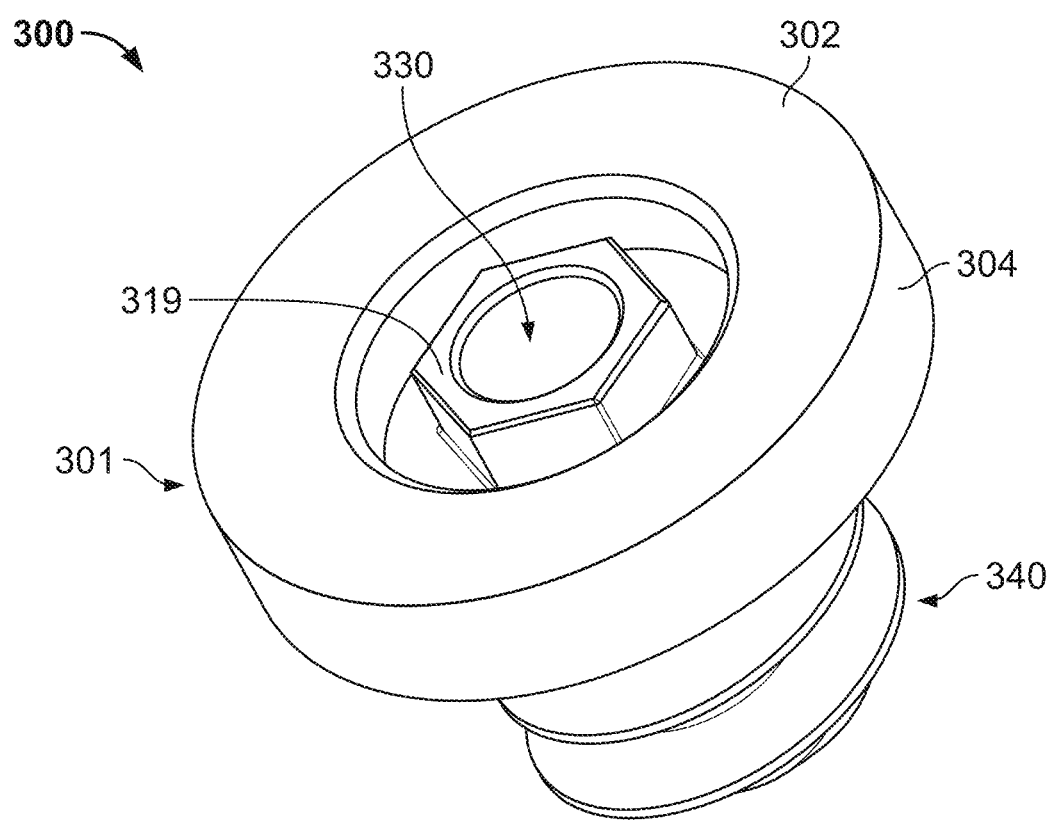
FIG. 10 is a top perspective view of an embodiment according to another aspect of the disclosure.
Figure 11:
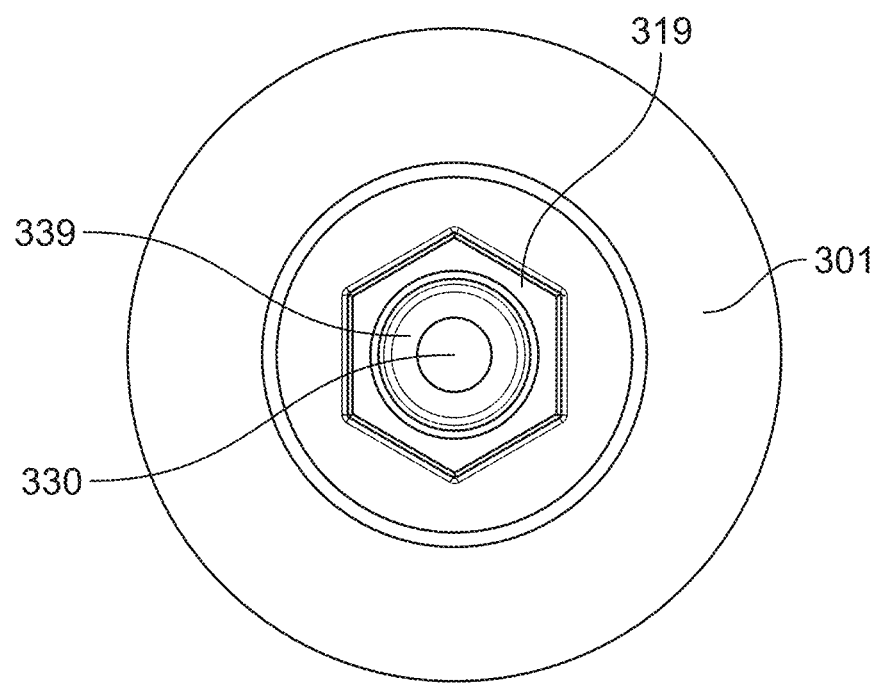
FIG. 11 is a top view of the base of FIG. 10.
Figure 12:
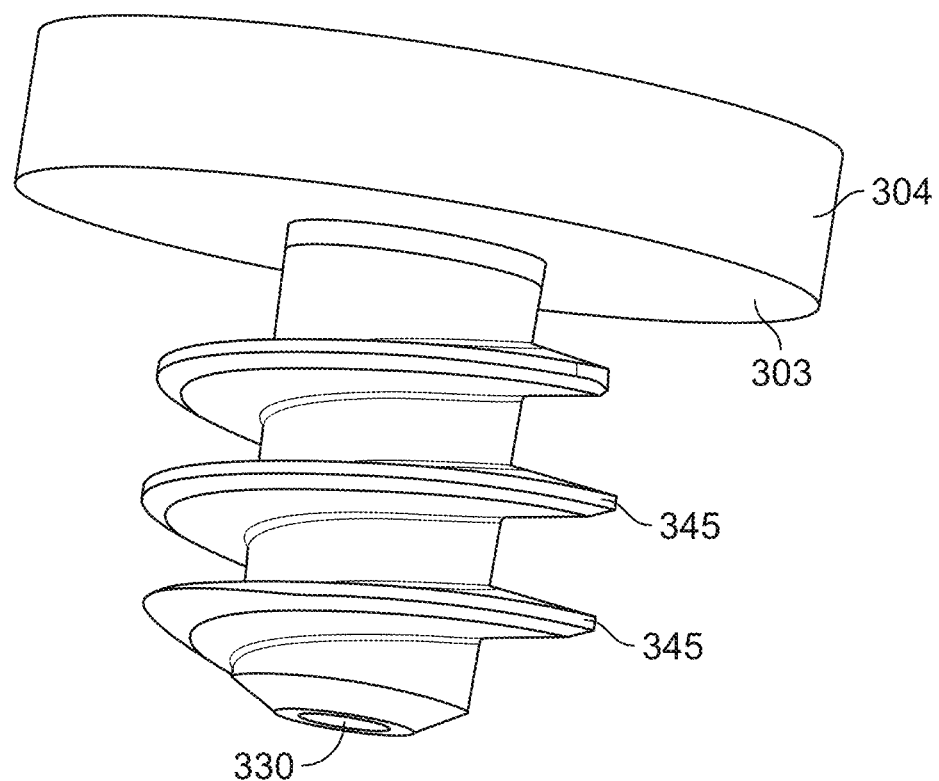
FIG. 12 is a side perspective view of the base of FIG. 10.
Figure 13:
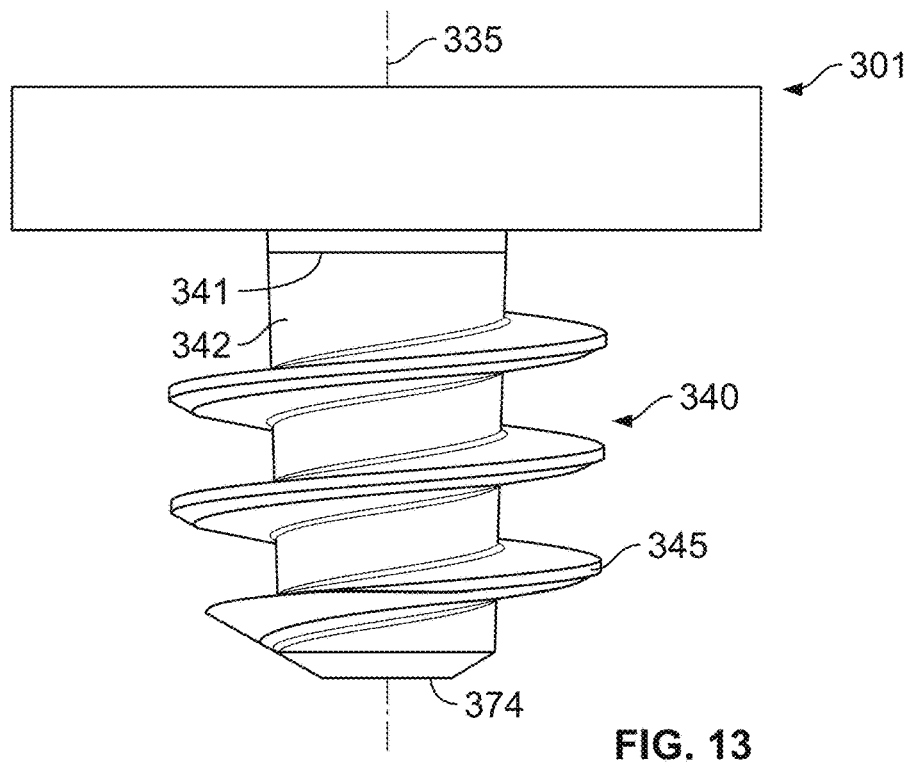
FIG. 13 is a side view of the base of FIG. 10.
Figure 14:
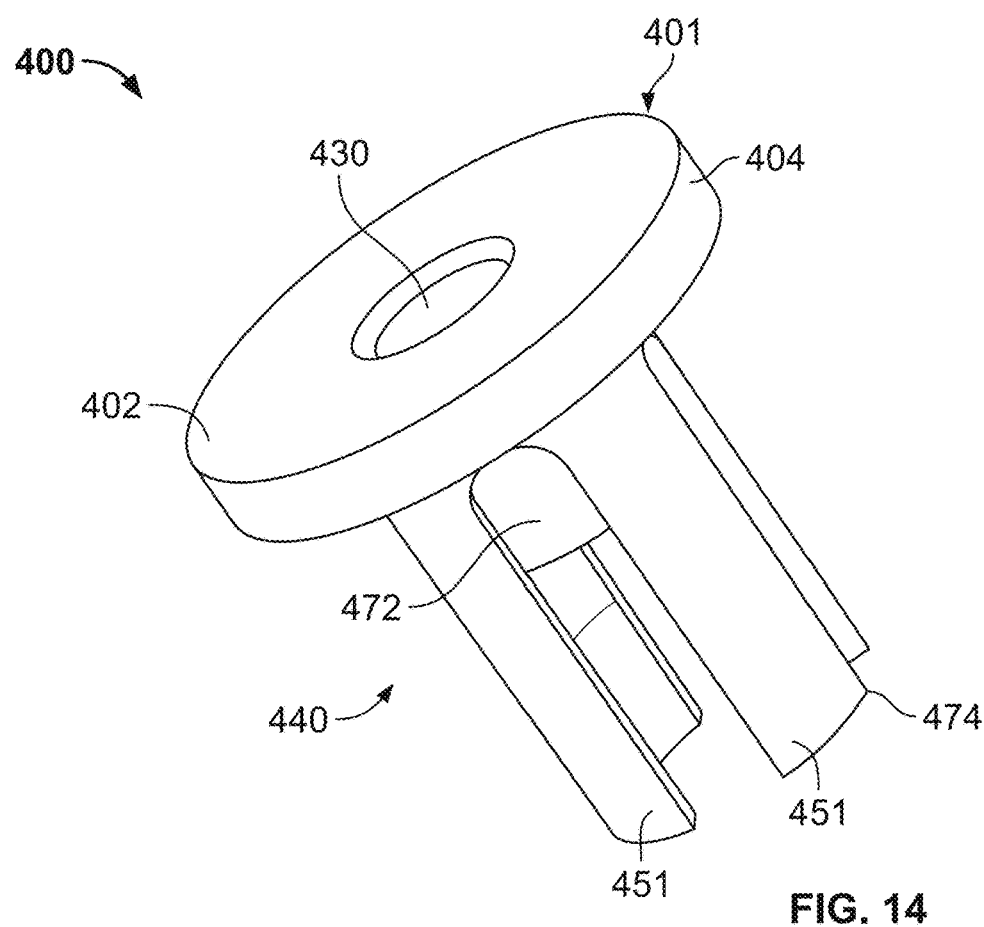
FIG. 14 is a top perspective view of a base of a shoulder implant according to another aspect of the disclosure.

As shown in FIGS. 10 and 11, base 300 includes a socket, which in the illustrated embodiment is a hex member 319, positioned within an interior cavity of collar 301. Hex member 319 defines an opening 330 which is adapted to receive an articulating component (not shown) of the stemless implant. In the illustrated embodiment, opening 330 extends from proximal end surface 302 of collar 301 along longitudinal axis 335 to annular proximal surface 339 of anchor 340, where the diameter of the opening decreases. With the decreased diameter, opening 330 then extends from annular proximal surface 339 of anchor 340 along longitudinal axis 335 to second end 374. Thus, anchor 340 of base 300 may be cannulated. In this way, base 300 may be inserted through a pilot wire, such as a K-wire, to help provide more accurate placement of base member 300 within a prepared portion of the bone. As illustrated, hex member 319 has a hexagonal shape. The proximal end of hex member 319 may be substantially flush with the proximal surface 302 of collar 301, although in some embodiments it may extend either proximally or distally of proximal surface 302. A driver (not shown) having a mating internal hex member may engage hex member 319. This may cause rotation of hex member 319 and base 300 which may provide torque for fixation of base member 300 in the bone. It should be understood that although the socket is illustrated as having a hexagonal shape, any shape suitable for transmitting torque from a correspondingly shaped driver tool may be suitable.

Anchor 340 includes outer wall 342 extending from first end 341 toward second end 374. When used as part of a shoulder implant system, anchor 340 may be configured to be driven into the metaphyseal cancellous bone of the humerus and to facilitate engagement between base 300 and the bone for fixation. Threads 345 extend around outer wall 342 of anchor 340 and may be disposed helically in a screw-like configuration. When the driver (not shown) engages hex member 319 and causes rotation of base 300, threads 345 may engage the bone and may provide greater fixation of the base to the bone.

FIGS. 14-17 show base 400 of a stemless implant according to another aspect of the disclosure. Base 400 generally includes collar 401 coupled with central anchor 440. Collar 401 may be generally cylindrical or annular and includes a proximal end surface 402, a distal bone engaging-surface 403, and a side flange surface 404. Proximal end surface 402 may be flat as shown, but in other embodiments it may be inclined or sloped. Side flange surface 404 may have a uniform height, the height measured from distal to proximal ends of side flange surface 404, or the height may vary along proximal end surface 402. Collar 401 may have other shapes, such as generally oblong and may include additional holes for use with insertion/extraction tools and/or for accepting sutures, similar to holes described in embodiments above.

Figure 15:
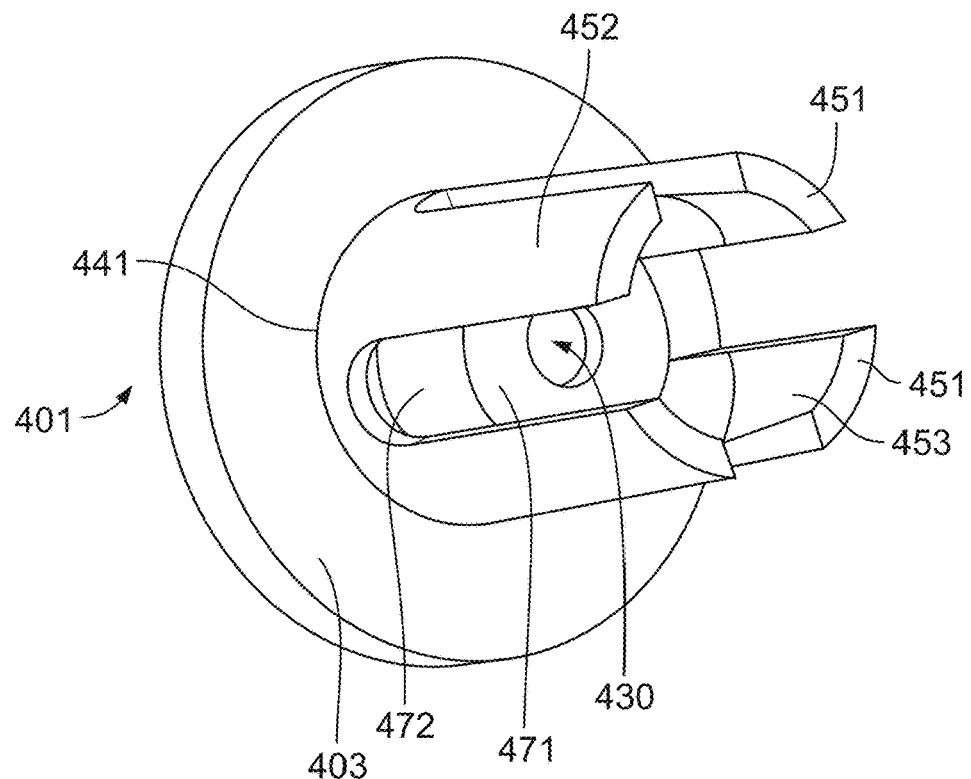
FIG. 15 is a bottom perspective view of the base of FIG. 14.
Figure 16:
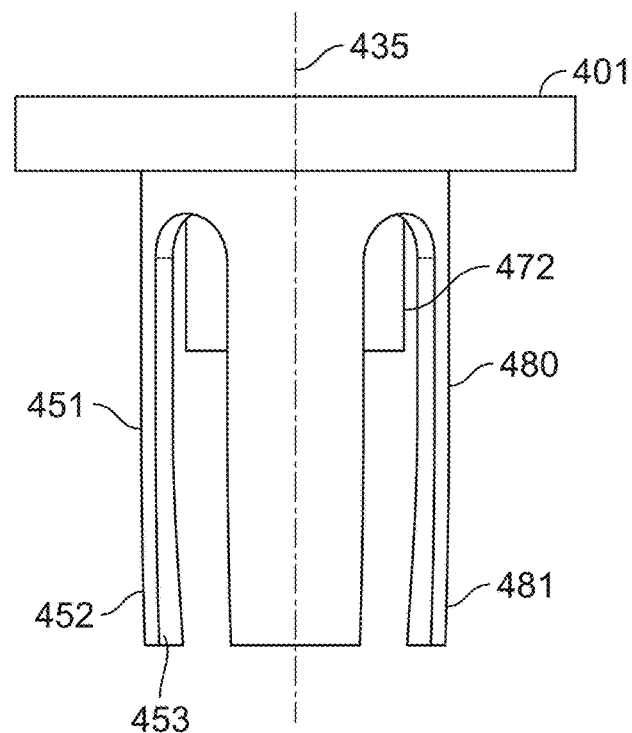
FIG. 16 is a side view of the base of FIG. 14.

Base 400 includes central anchor 440 coupled to collar 401 at a first end 441 and extending distally from the collar along a longitudinal axis 435 to a second end 474. As illustrated, anchor 440 may include flanges 451 extending from bone-engaging surface 403, substantially parallel to longitudinal axis 435, to second end 474 of the anchor. As shown in FIGS. 15 and 16, flanges 451 may include outer surfaces 452 and inner surfaces 453. Inner surfaces 453 may be slightly concave along at least a portion of the inner surfaces. Inner surfaces 453 may include internal threads along at least a portion thereof. Flanges 451 may include a straight portion 480 and a tapered portion 481. Straight portion 480 may extend generally parallel to longitudinal axis 435, whereas tapered portion 481 may taper radially inwardly from the distal end of straight portion 480 to second end 474 of anchor 440 such that inner surfaces 453 nearer second end 474 may be radially closer to longitudinal axis 435 than a point on inner surface nearer straight portion 480. Likewise, outer surfaces 452 nearer second end 474 may be radially closer to longitudinal axis 435 than a point on the outer surface nearer straight portion 480. However, the degree of the taper of the outer surfaces 452 and inner surfaces 453 of flanges 451 may be different. For example, the taper of outer surfaces 452 may be less than the taper of the inner surfaces.

Anchor 440 includes support 472, which may be a cylinder, extending from bone-engaging surface 403 of collar 401 along longitudinal axis 435 to a distal end surface 471 of the cylinder. Support 472 may be positioned generally centrally on bone-engaging surface 403.

Base 400 includes opening 430 extending from proximal end surface 402 of collar 401 along longitudinal axis 435 to a distal end surface 471 of support 472. The diameter of opening 430 may decrease near the distal end of support 472. In the illustrated example, base 400 may be adapted to couple to a proximal humerus of a patient, with a prosthetic humeral head adapted to couple to the base via opening 430, the prosthetic humeral head intended to articulate with a native or prosthetic glenoid of the shoulder joint. Although opening 430 may have any shape that suitably mates with the corresponding portion of the prosthetic humeral head, in one example a taper such as a Morse taper may be used to lock the prosthetic humeral head within opening 430.

Figure 17:
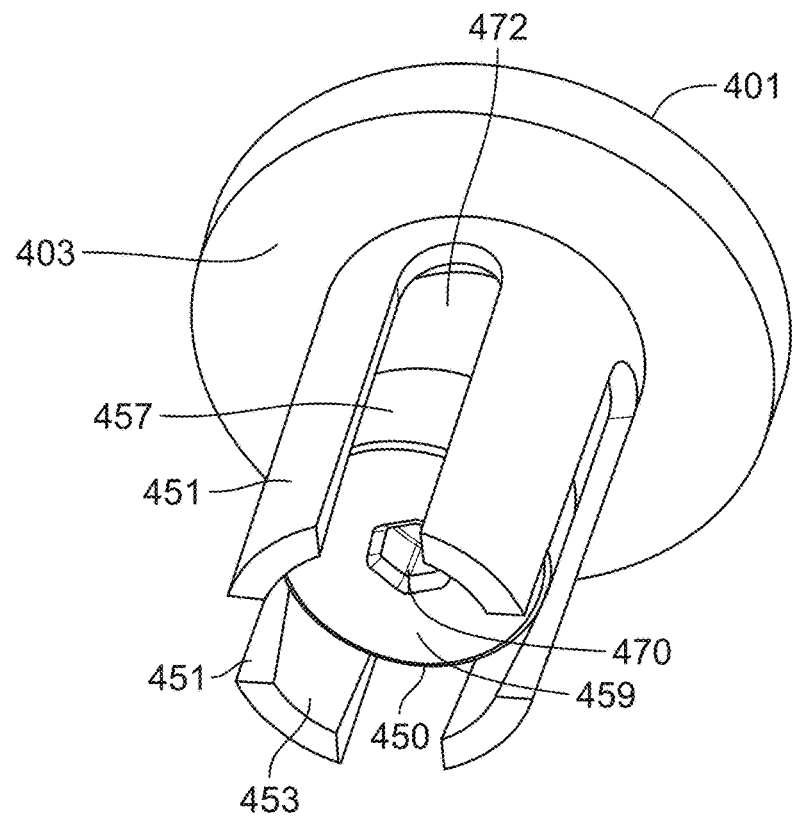
FIG. 17 is a bottom perspective view of the base of FIG. 14 with a nut assembled thereto.
Figure 18:
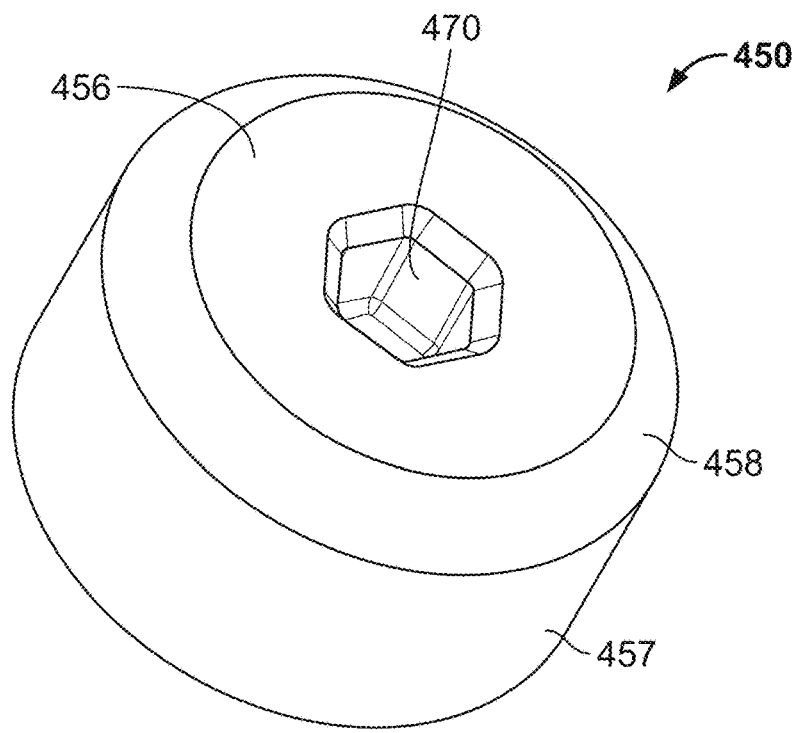
FIG. 18 is a top perspective view of the nut of the base of FIG. 14.

As shown in FIGS. 17 and 18, anchor 440 may include screw nut 450. Nut 450 may include a proximal end surface 456, a side flange surface 457, an angled surface 458, and a distal end surface 459. Nut 450 may be generally cylindrical. In the illustrated embodiment, nut 450 includes angle surface 458; however, in other embodiments side flange surface 457 may connect with proximal end surface 456 and there may not be an angled surface. Nut 450 may include two openings 470 extending along longitudinal axis 435 from respective proximal and distal end surfaces 456 and 459. Openings 470 may not connect and may remain two distinct openings. Openings 470 may have a hexagonal shape to matingly engage with a driver for rotation of the nut and movement in a distal direction, although any shape for transmitting torque from a correspondingly shaped driver may be suitable. Distal opening 470 may be used for manufacturing assembly. A tool (not shown) may couple with distal opening 470 to insert nut 450 into anchor 440. Nut 450 may include external threads on the outer circumference of side flange surface 457. The threads may be adapted to matingly engage the threads on inner surfaces 453 of flanges 451. Nut 450 may maintain contact with at least a portion of inner surfaces 453 of the flanges.

Flanges 451 of anchor 440 may be expandable. The diameter of nut 450 across side flange surface 457 may be greater than the diameter across the inner surfaces 453 of tapered portion 481 of the flanges. During an implantation procedure, base 400 may be implanted into a bone, such as a proximal humerus, with nut 450 positioned in contact with or adjacent to support 472. In this position, flanges 451 are in an insertion condition (which may also be referred to as a removal condition) in which the diameter of anchor 440 is in a constrained or contracted condition. After implanting anchor 440 into the proximal humerus, for example in cancellous bone, a driver may be passed through opening 430, with an end of the driver engaging the opening 470 of nut 450. The surgeon may manually or otherwise rotate the driver to cause corresponding rotation of nut 450, while the remainder of base 400 remains stationary with respect to the bone. Rotation of nut 450 results in external threads of the nut engaging internal threads of the flanges 451 so that the nut translates distally toward tapered portion 481 of flanges 451. As the nut 450 is driven distally, it engages tapered portion 481 of flanges 451. Because the nut 450 has a larger diameter than the internal diameter of flange 451 when the flanges 451 are in the implanted condition, the nut forces the flanges to expand outwardly into an expanded or implanted condition. This expansion of flanges 451 into the cancellous bone may provide for enhanced fixation between base 400 and the bone, for example by increasing the force required for the base to be pulled out of the bone.

At least one flange 451 may include a stop (not shown) near the distal end of the flanges. The stop is designed to limit the distance nut 450 can translate distally. In another example, a driver (not shown) having a positive stop may be used to translate the nut while preventing translation beyond the intended position. The driver may be used alone or in conjunction with a stop on the flanges. In this way, the nut 450 will translate distally only to an intended location.

Figure 19:
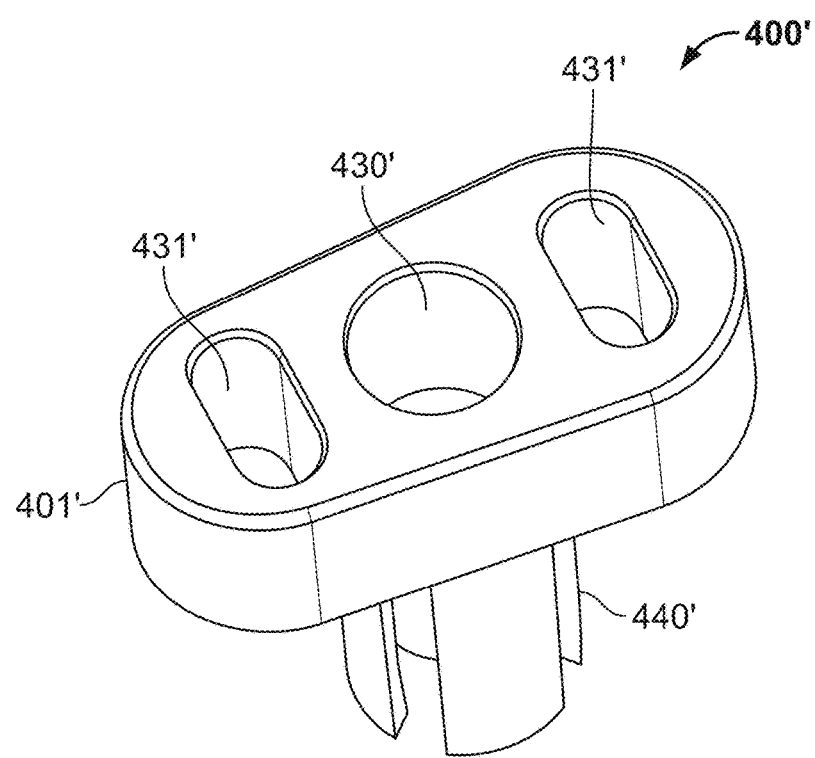
FIG. 19 is a top perspective view of an alternate embodiment of the base of FIG. 14.
Figure 20:
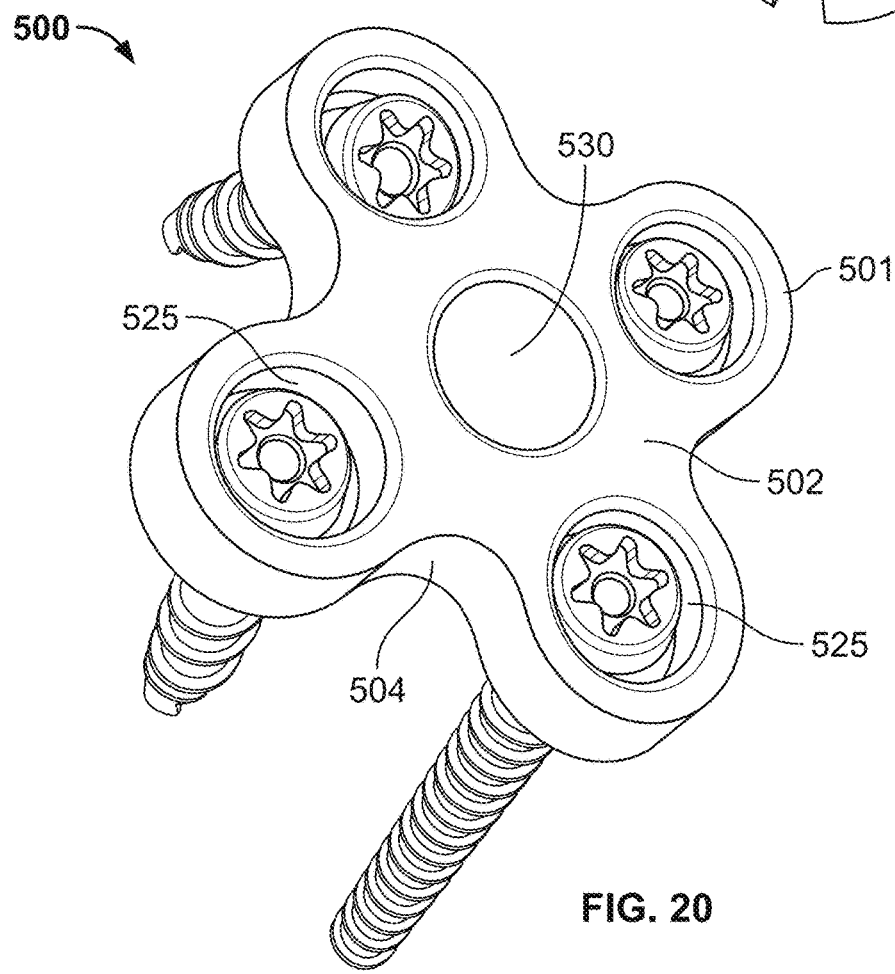
FIG. 20 is a top perspective view of a base of a shoulder implant according to another aspect of the disclosure.

FIG. 19 illustrates base 400' that is identical to base 400 in most respects. For example, anchor 440' of base 400' may be completely identical to anchor 440, and may include a screw nut identical to screw nut 450. Thus, those components are not described again. However, collar 401' of base 400' may have an alternate shape. Whereas collar 401 of base 400 is illustrated as being cylindrical, collar 401' may be oblong with two substantially straight portions on the anterior and posterior sides of the collar, with two substantially rounded portions on the medial and lateral sides of the collar. The width of collar between the anterior and posterior ends may gradually increase from the medial rounded portion toward the lateral rounded portion, which may better correspond to the native anatomy of the proximal humerus. In addition to opening 430', which may be identical in form and function to opening 430, collar 401' may include additional openings 431' that may be used to mate with an insertion or extraction tool (not shown) or for other suitable purposes, such as for receiving sutures, etc.

It should be understood that bases 300 and 400 may be formed of any suitable surgical grade material, including, for example, titanium alloys and/or other biocompatible metals, metal alloys, and/or plastics. Further, although holes 211 and 213 are only described in connection with base 200, similar or identical holes may be provided in bases 300 and 400 for similar purposes.

For each base described above, if being used in a shoulder joint application for coupling to a prosthetic humeral head, the proximal humerus is generally prepared to have a substantially planar surface prior to implantation of the base. As noted earlier, each base described herein may be referred to as a stemless base. The collar of each base, however, may have a perimeter that is substantially similar to, or fits within, the perimeter of the proximal end of a typical stemmed base (not shown) for a more traditional shoulder implant. With this configuration, if a surgeon begins preparing a patient's proximal humerus to accept any of the bases described herein, and it is determined that a stemless implant will ultimately not be suitable for use in the patient, the surgeon may instead use a traditional stem in the patient, even though the proximal humerus was prepared for a stemless implant. In other words, the geometries of the bases described herein, and in particular the collars of the bases, allow a surgeon a contingency plan of switching to a traditional stemmed shoulder implant mid-procedure, if such a contingency plan is deemed preferable and/or necessary.

FIGS. 20-23 show base 500 of a stemless implant according to another aspect of the disclosure. Base 500 generally includes collar 501 coupled with central anchor 540. Collar 501 may have a generally rounded cruciform shape, although in other examples, the collar may have other shapes including oblong or annular. Collar 501 includes a proximal end surface 502, a distal bone engaging-surface 503, and a side flange surface 504. Proximal end surface 502 may be flat as shown, but in other embodiments it may be inclined or sloped. Side flange surface 504 may have a uniform height, the height measured from distal to proximal ends of side flange surface 504, or the height may vary along proximal end surface 502. Distal bone-engaging surface 503 may include a porous surface, for example porous titanium alloy, across all or a portion of its surface to provide better fixation of the implanted base with the bone.

Figure 21:
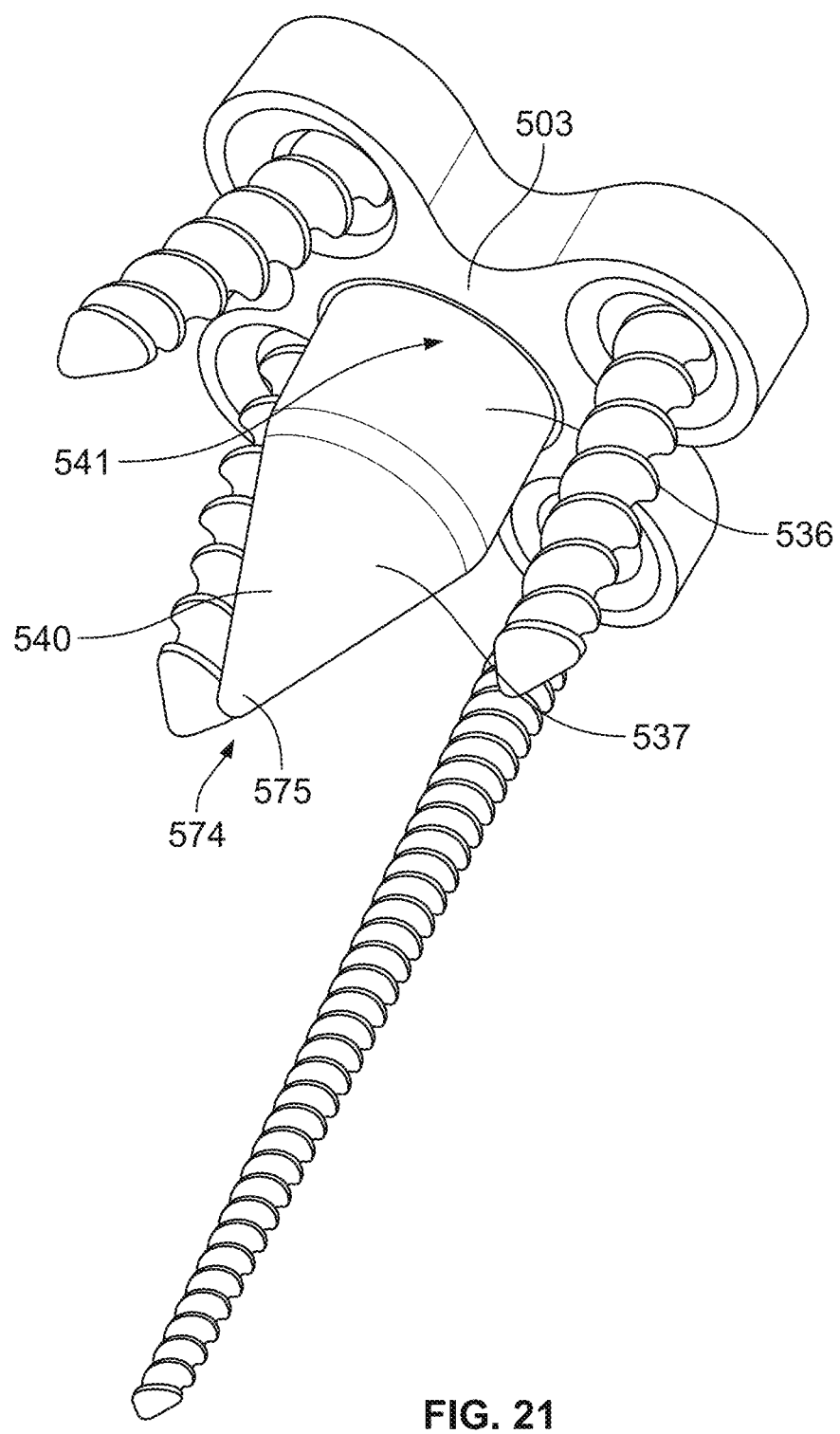
FIG. 21 is a bottom perspective view of the base of FIG. 20.
Figure 22:
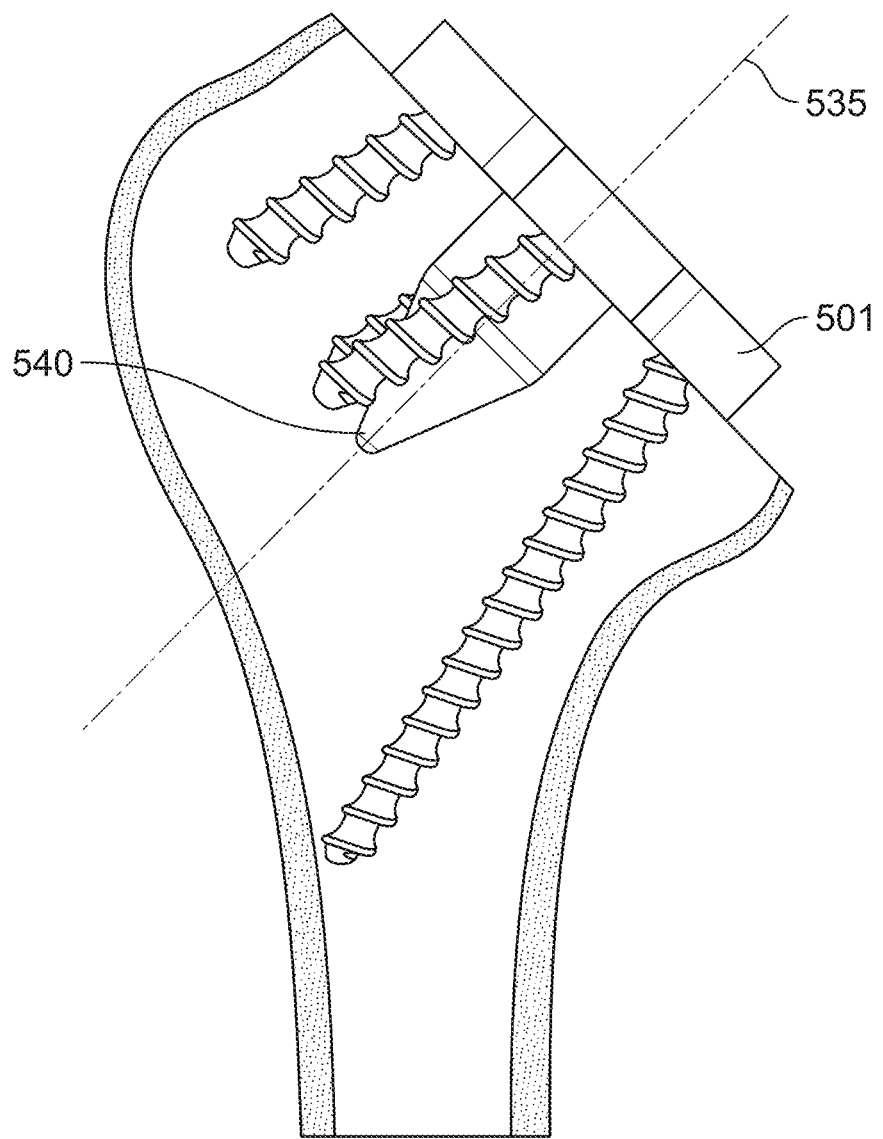
FIG. 22 is a cutaway view of the base of FIG. 20 implanted on a proximal humerus.
Figure 23:
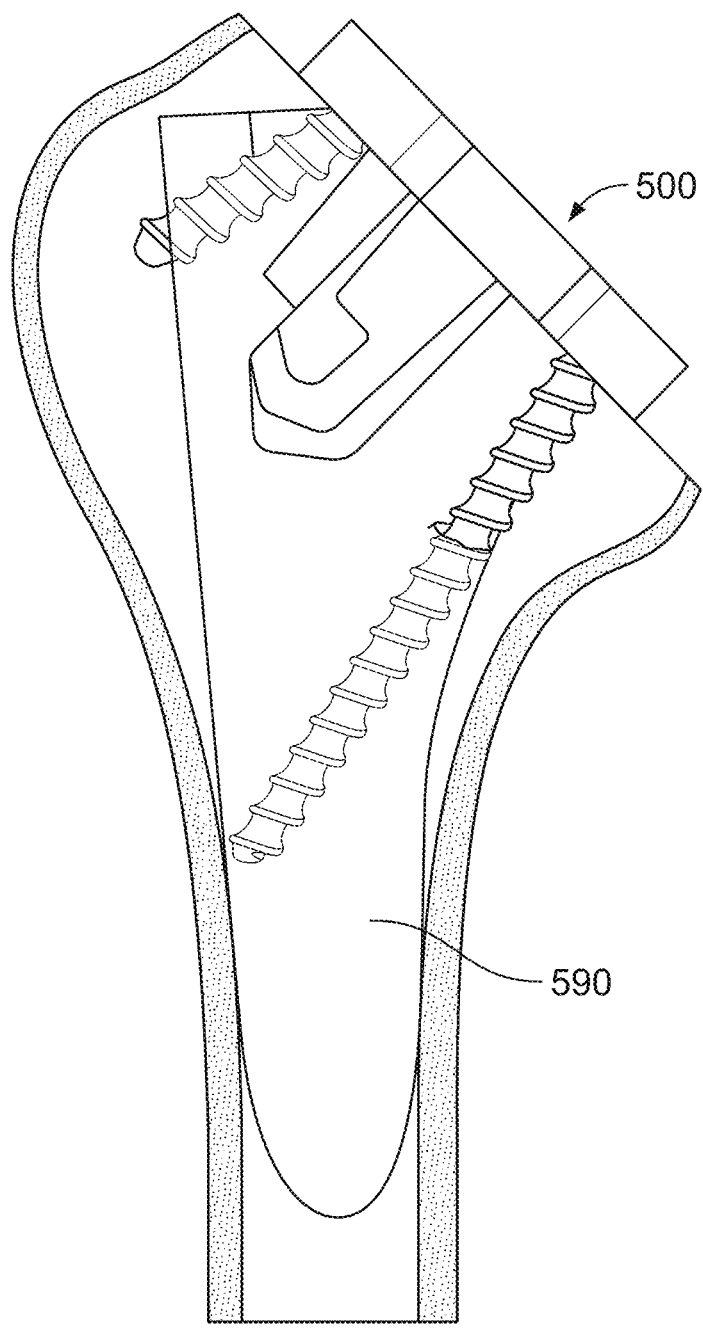
FIG. 23 is a schematic representation comparing an implant profile of the base of FIG. 20 to an implant profile of a tapered stem in a proximal humerus.
Figure 24:
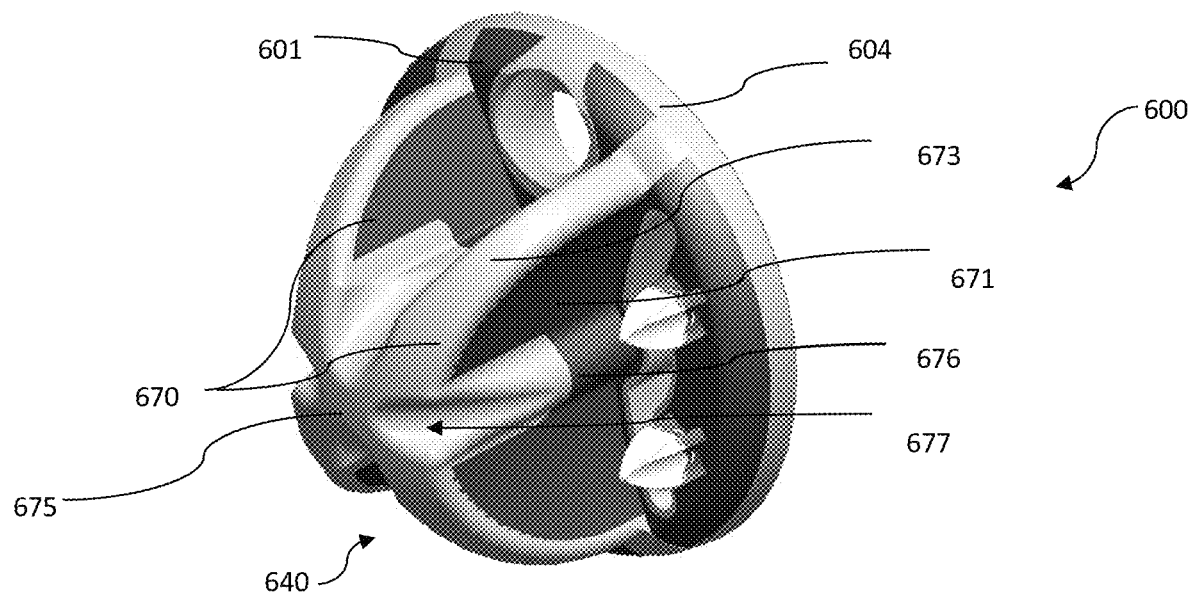
FIG. 24 is a side perspective view of a base of a shoulder implant according to another aspect of the disclosure.

Collar 501 includes at least one hole 525 extending from proximal end surface 502 to distal bone-engaging surface 503. The holes 525 are each adapted to receive a screw. In the illustrated embodiment, there are four holes 525 and four screws, although there can be more or fewer holes and/or screws. The screws may be variable angle locking screws capable of being inserted through holes 525 at variable angles, with the heads of the screws having locking threads to mate with corresponding locking threads in the holes. The screws may engage the bone to provide fixation of base 500 in the bone. As shown in FIGS. 21-23, the screws may have varying lengths to accommodate bone purchase to help with fixation, although any combination of screw lengths may be appropriate. In the illustrated embodiment, the medial screw has a length that is greater than the length of central anchor 540.

Base 500 includes central anchor 540 coupled to collar 501 at a first end 541 and extending distally from the collar along a longitudinal axis 535 to a second end 574. In the illustrated embodiment, anchor 540 has a straight portion 536, which may be cylindrical, and a tapered portion 537, which may be conical or frustoconical. Tapered portion 537 is tapered along longitudinal axis 535 so that the proximal end of the tapered portion has a relatively large diameter, with the diameter of the anchor generally narrowing toward second end 574 until the anchor terminates in distal tip 575.

As with previous embodiments of the bases, base 500 may further define an opening 530. Opening 530 may extend distally along longitudinal axis 535 from proximal surface 502 of collar 501. Opening 530 may extend partially or fully through anchor 540 along longitudinal axis 535 or it may be shallow and extend only into collar 501. A humeral head component (not shown) may be placed within opening 530 and attached thereto, for example by a taper lock such as a Morse taper. The humeral head component may be attached by any known securement means including screw or friction fit. Base 500 may include additional holes for use with insertion/extraction tools and/or for accepting sutures, similar to holes described in embodiments above.

FIG. 22 shows base 500 implanted within a humeral bone with variable angle locking screws. The benefit of using screws of different lengths is particularly well illustrated in FIG. 22. For example, a screw that engages a hole 525 on the medial side of collar 501 may be longer than the other screws, as there may be a greater depth of bone available in this area.

FIG. 23 illustrates base 500 implanted into a humeral bone, similar to FIG. 22. However, FIG. 23 also illustrates the expected implant profile of a traditional stem 590 of a stemmed shoulder implant. As can be seen by the superimposition of base 500 with the profile of a traditional stem 590, the base 500 may be designed so that much or all of the portion of the base implanted into the humerus would occupy space that would also be occupied by a traditional stem 590, if a traditional stem 590 were implanted into the humerus. As a result, if a humerus is prepared to accept base 500, and it is determined that a more traditional shoulder implant with stem 590 would be desirable, the surgeon may choose to use traditional stem 590 instead. It should be understood that this concept may apply to each of the other bases described herein, so that a surgeon may prepare a proximal humerus to accept any of the bases described above or below (e.g. bases, 100, 200, 300, 400, 600, 600', 600", 900, etc.) and may choose mid-procedure to switch to a tapered stem 590 without having unnecessarily removed any bone. Such a change in procedure may become desirable, for example, if the surgeon determines that the stemless base would not be able to achieve suitable fixation with the humerus, for example because the bone quality is low.

FIGS. 24-28 show base 600 similar to bases 200 in many respects, the similar or identical features of which will not be described again here. In the illustrated embodiment, base 600 has a collar 601 that is generally annular, and may be circular, although in other examples, the base can be any shape, such as triangular, trapezoidal, etc. Base 600 includes curved side wall 604 which extends between proximal surface 602 and bone-engaging surface 603. The curve of side wall 604 may help to decrease the amount of bone removed during surgery. Proximal surface 602 may include opening 630 which is adapted to receive an articulating component (not shown) of the stemless implant.

Base 600 includes central anchor 640 extending distally from bone-engaging surface 603 to distal end 675. Anchor 640 includes a plurality of ribs 670, each rib projecting radially outward of distal end 675 and extending to bone-engaging surface 603. Ribs 670 extend along bone-engaging surface 603 to a position in close proximity to or adjacent to side wall 604. Each rib 670 includes two lateral side walls 671 and curved outer surface 673 between the two lateral side walls. Lateral side walls 671 may be flat, concave, and/or convex. The outer surface 673 is rounded which may provide more surface to create bone in-growth after implantation of the base 600.

Figure 25:
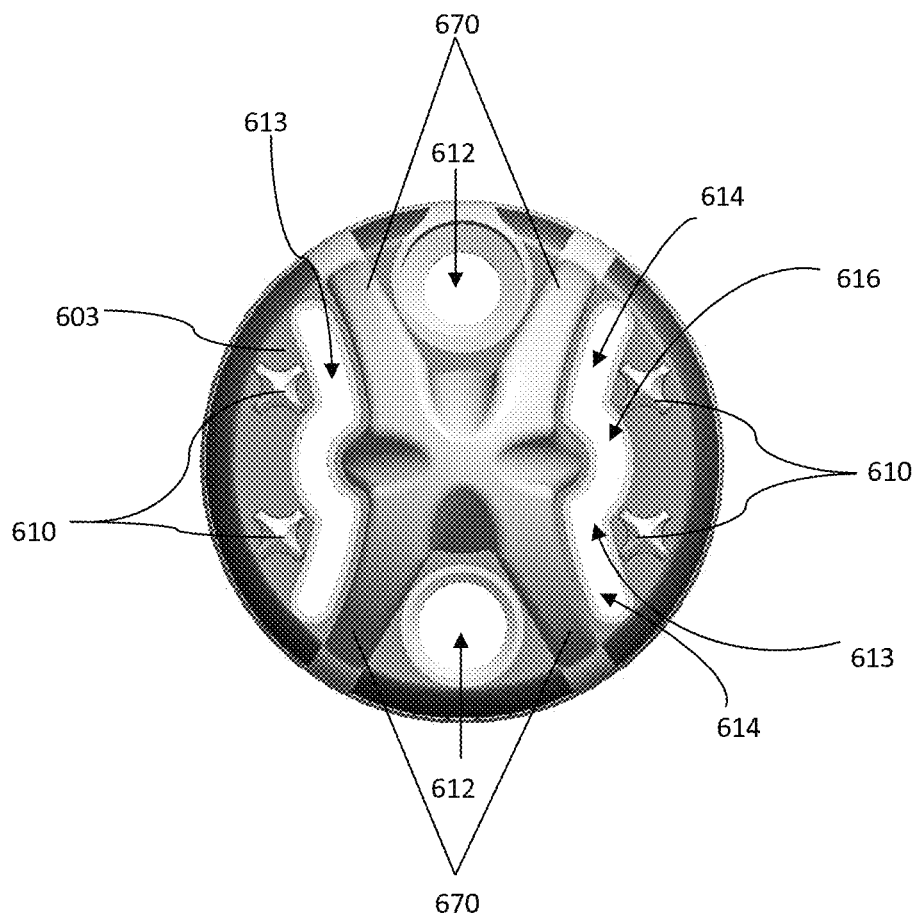
FIGS. 25-26 are the same bottom views of the base of FIG. 24, with the two figures identifying different features of the base.
Figure 26:
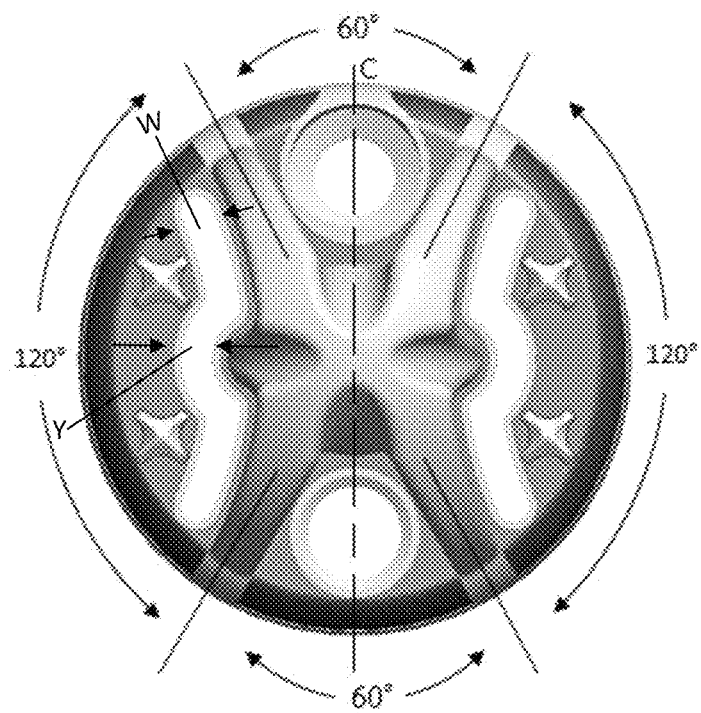

Referring to FIGS. 25-26, base 600 may include four ribs 670 that form a general "X" shape. As shown in FIG. 26, two pairs of adjacent ribs may be oriented about 60 degrees apart from one another, and two other pairs of adjacent ribs may be oriented about 120 degrees apart from one another. However, it should be understood that other angles between the pairs of adjacent ribs may be suitable.

Anchor 640 includes surfaces 676 extending from distal end 675 to bone-engaging surface 603. In the illustrated embodiment, each surface 676 is positioned between two ribs 670, although in other examples there may be more or fewer surfaces 676. In the illustrated embodiment, surfaces 676 are rounded and include grooves or channels 677 positioned near the distal end 675 of the base and extending in a direction toward bone-engaging surface 603. Channel 677 tapers inwardly as it extends in the direction toward distal end 675. Channel 677 may help facilitate bone in-growth after base 600 is implanted.

Figure 27:
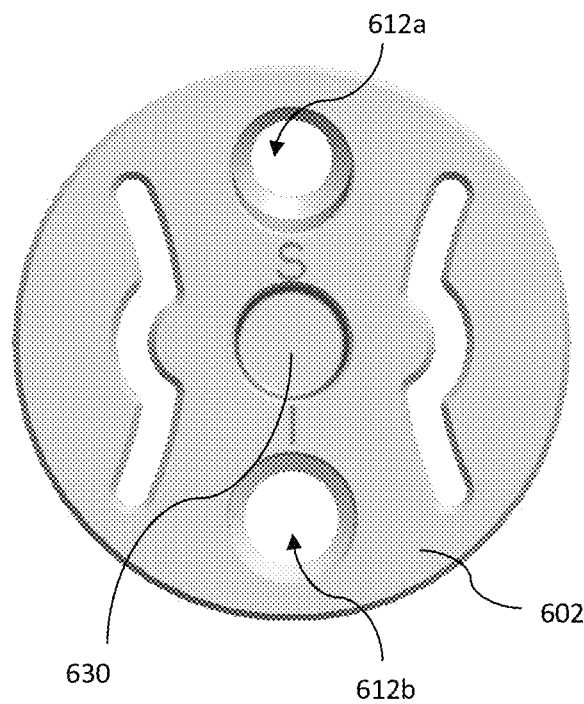
FIG. 27 is a top view of the base of FIG. 24.
Figure 28:
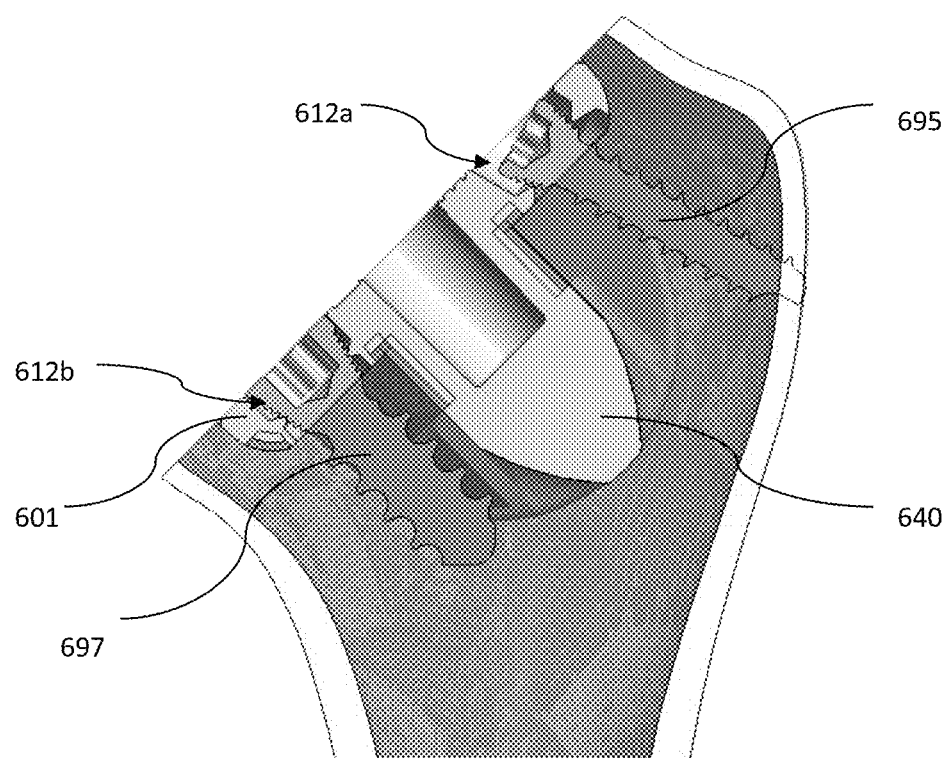
FIG. 28 is a schematic representation of the base of FIG. 24 implanted in a humerus.

Base 600 may include holes 612 extending from proximal surface 602 to bone-engaging surface 603. In the illustrated embodiment, base 600 includes two holes 612, each positioned between the ribs 670 that are spaced substantially 60 degrees apart from one another. In other examples, however, there may be more or fewer holes 612 on the base 600. Additionally, holes 612 may have the same diameter, or as in the illustrated embodiment, the holes 612 may have different diameters. As shown in FIGS. 26-28, superior hole 612a has a smaller diameter than inferior hole 612b. Superior hole 612a is configured to receive variable angle screw 695, the threaded diameter of which can be from about 3 to about 6 millimeters (mm) and is preferably about 4.5 mm Additionally, variable angle screw 695 can have about a 15 degree pre-tilt angle. Inferior hole 612b is configured to receive fixed angle screw 697, the threaded diameter of which can be from about 5 to about 7 mm and is preferably about 6.5 mm Variable angle screw 695 can have a longer shaft than fixed angle screw 697. For example, variable angle screw 695 may have a threaded shaft of about 24 mm, and fixed angle screw may have a threaded shaft of about 20 mm.

When implanted, base 600 is preferably oriented such that superior hole 612a is positioned superior to inferior hole 612b in relation to the shoulder. The inferior hole having a larger diameter may allow for a greater degree of fixation in the better quality bone having greater density.

Base 600 includes pegs 610 extending distally from bone-engaging surface 603. Pegs 610 may be shaped identically to pegs 210 of base 200. In the illustrated embodiment, there are two pairs of pegs 610 positioned radially outward of lateral side walls 671 of ribs 670. Each pair of pegs 610 is positioned between ribs 670 that are spaced about 120 degrees apart from one another. However, there may be more or fewer pegs 610, which may be larger or smaller. In some examples, base 600 may not include any pegs.

Like base 200, base 600 may include one or more enhanced fixation surfaces on portions of anchor 640 and bone engaging surface 603. The enhanced fixation surface may also be positioned on portions of pegs 610 and may extend onto side walls 604 of the base member. Generally, the enhanced fixation surface is positioned on proximal portions of the anchor 640 and the pegs 610. The enhanced fixation surface may be identical to enhanced fixation surface 259 of base 200 and may take the form of a porous metal surface, such as a porous titanium alloy, including Tritanium® by Howmedica Osteonics Corporation.

Base 600 includes continuous chisel slots 613 extending through bone-engaging surface 603 to proximal surface 602. Chisel slots 613 are positioned near the connection of ribs 670 and surfaces 676 with bone-engaging surface 603. Thus, in the illustrated embodiment, chisel slots 613 include elongated portions 614 that track near ribs 670 and substantially curved portions 616 that track near surfaces 676. Elongated portions 614 may be substantially straight or may exhibit a curved shape. Each chisel slot 613 may form a substantially "M" shape with each chisel slot including two elongated portions 614 and one curved portion 616 in between the two elongated portions. Elongated portions 614 track adjacent rib 670, and extend in a direction that is about 30 degrees from a central axis C of the base that extends through the center of both holes 612. Each elongated portion 614 has a width W, and the curved portion 616 has a width Y, the widths W and Y may be substantially equal or they may be different. Additionally, in an alternative embodiment, the two elongated portions 614 of each chisel slot 613 may have different widths from each other.

Chisel slots 613 are sized and positioned to facilitate a revision procedure after base 600 has been implanted into a patient for an amount of time. In the illustrated embodiment, chisel slots 613 are positioned adjacent to pegs 610, surfaces 676 and lateral side walls 671 of the ribs 670. With this positioning of chisel slots 613, a surgeon may insert a tool into each slot 613 in order to chisel, ream, or otherwise cut away at bone that is adjacent to pegs 610, surfaces 676, and lateral side walls 671 of the ribs 670. This strategic positioning of the chisel slots 613 allows for loosening of the bone ingrowth on enhanced fixation surfaces, which provides for easier removal of the base 600 so that a new device may be implanted in its place. Additionally, the "M" shape of the chisel slots may provide more stability to a chisel tool as the shape of the chisel slot may require less bending of a correspondingly shaped tool.

Although not shown, base 600 may include a feature similar to fixation ring 238 of base 200. This fixation portion may surround all or a part of anchor 640 and may take the form of a recessed groove. The recessed groove may include an enhanced fixation surface to provide for better fixation of the base in bone.

Figure 29:
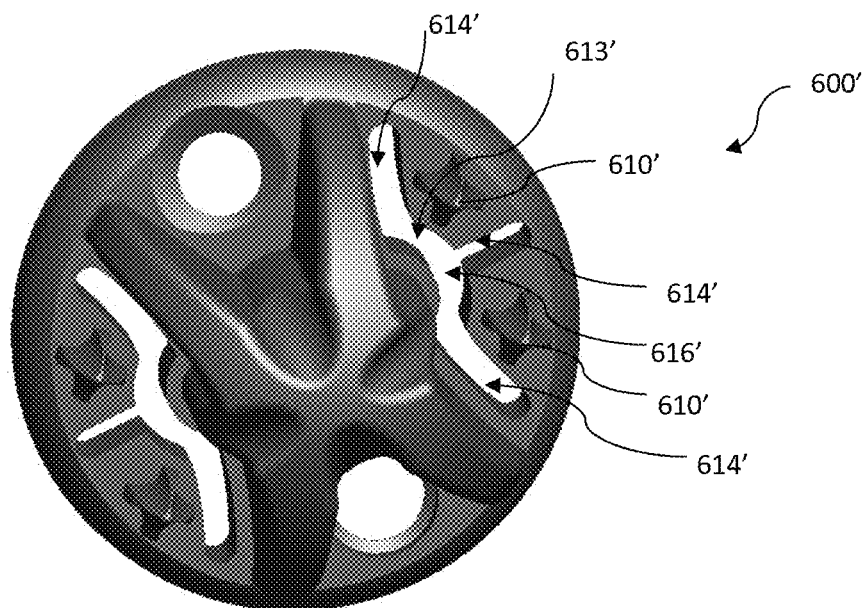
FIG. 29 is a bottom perspective view of a base of a shoulder implant according to another aspect of the disclosure.

FIG. 29 shows base 600' that is similar or identical to base 600 in most respects, the similar features of which will not be described here again. Each chisel slot 613' of the base 600' additionally includes a central elongated portion 614' extending radially outward from curved portion 616' and positioned between a pair of adjacent pegs 610'. Central elongated portion 614' may help during revision procedures, as further described below.

Figure 30:
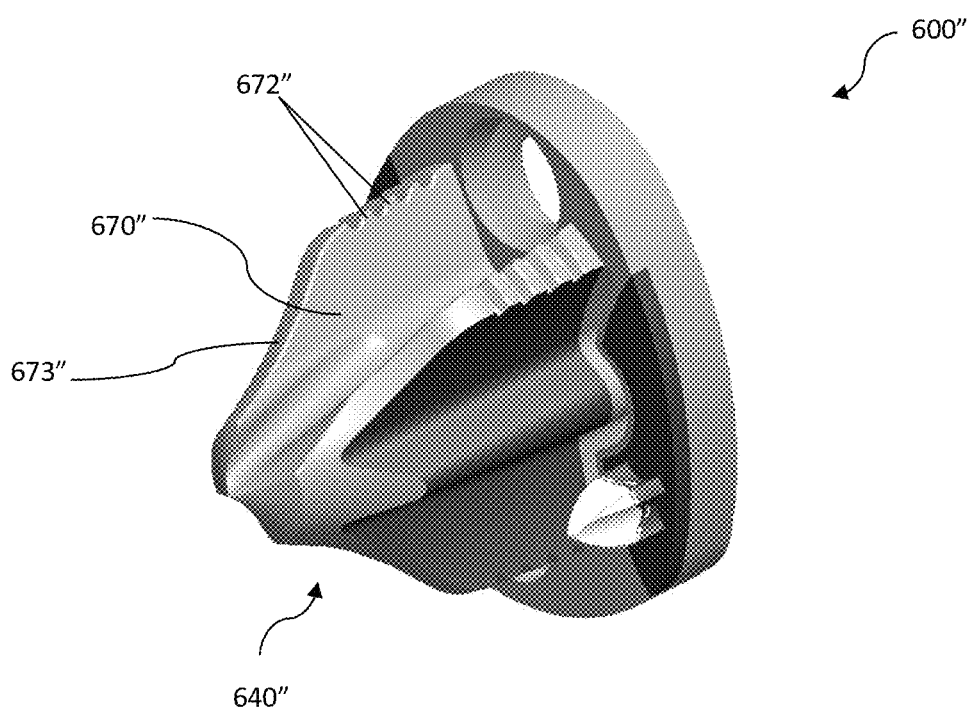
FIG. 30 is a side perspective view of a base of a shoulder implant according to another aspect of the disclosure.

FIG. 30 shows base 600" that is similar in many respects to bases 600, 600', the similar features of which will not be described again here. Base 600" includes anchor 640" having ribs 670". At least one rib 670" includes fish hook serrations 672" positioned on a portion of the curved outer surface 673". Serrations 672" are sharp slots positioned on the outer surface 673" of a rib 670" that create better bite into the bone during implantation of the base 600".

Figure 31:
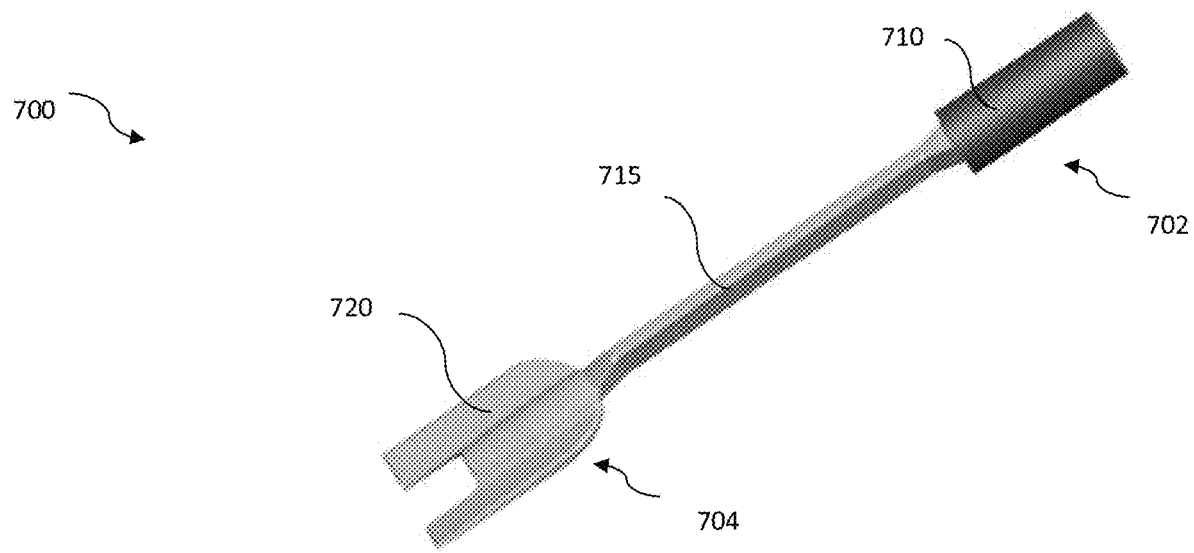
FIG. 31 is a side perspective view of a chisel tool according to another aspect of the present disclosure.
Figure 32:
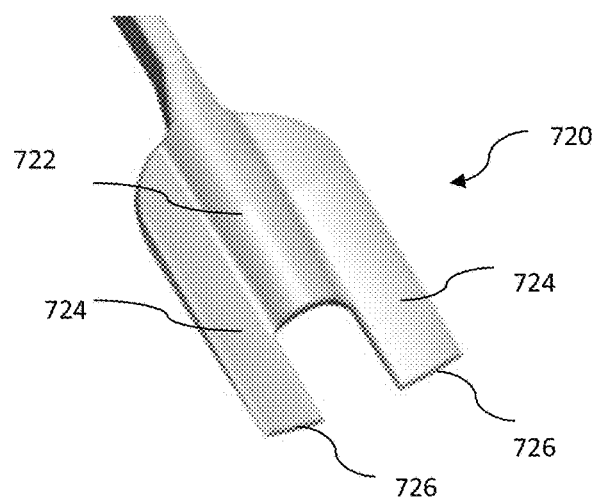
FIG. 32 is an enlarged front perspective view of a cutting structure of the chisel tool of FIG. 31.
Figure 33:
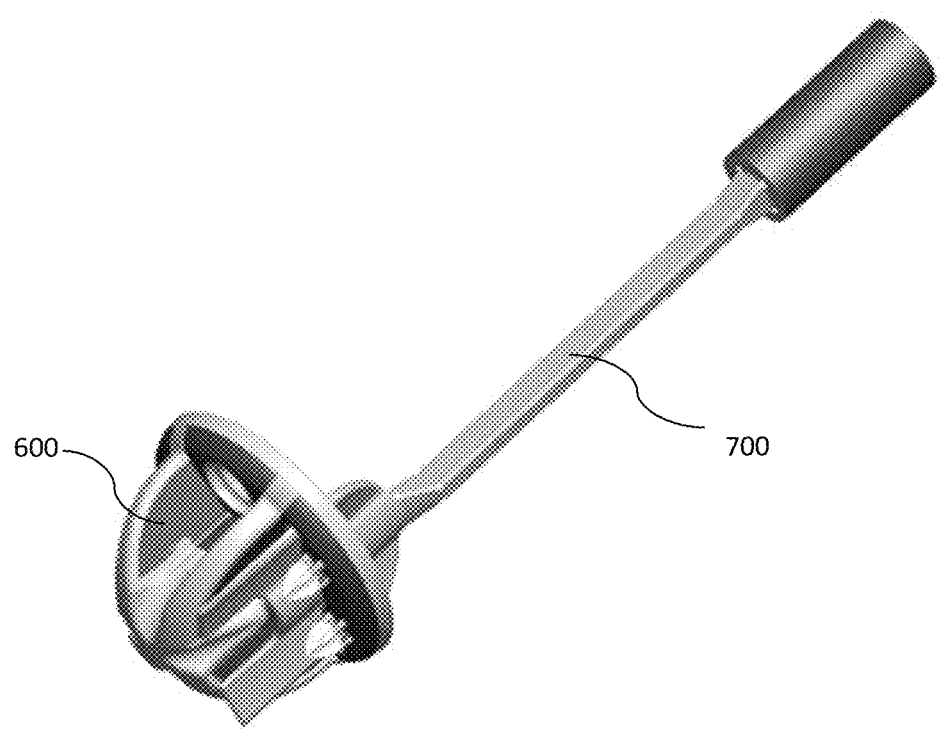
FIG. 33 is a side perspective view of the chisel tool of FIG. 31 in conjunction with the base of FIG. 24.
Figure 34:
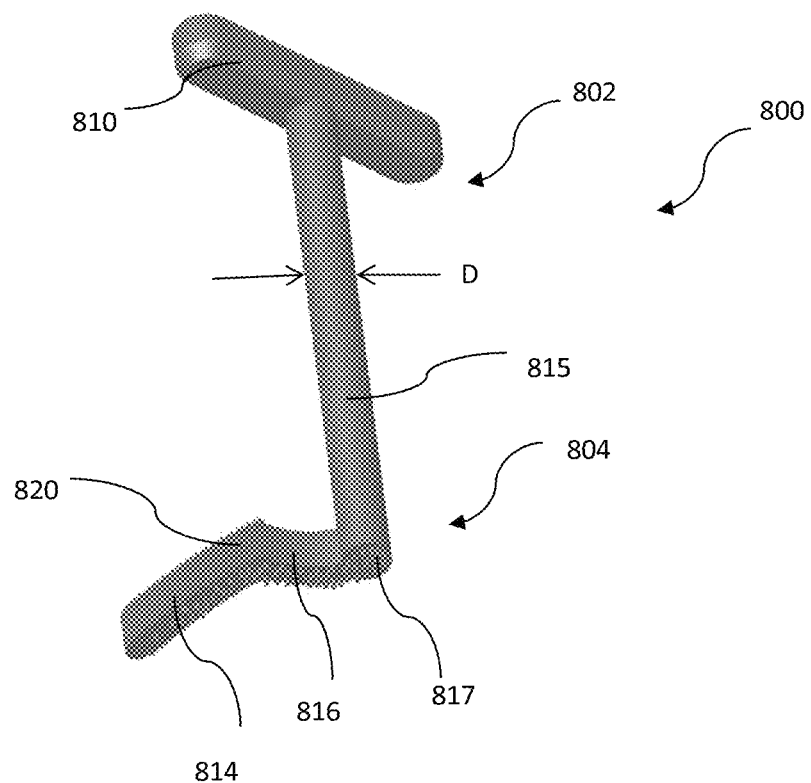
FIG. 34 is a side perspective view of a chisel tool according to another aspect of the present disclosure.
Figure 35:
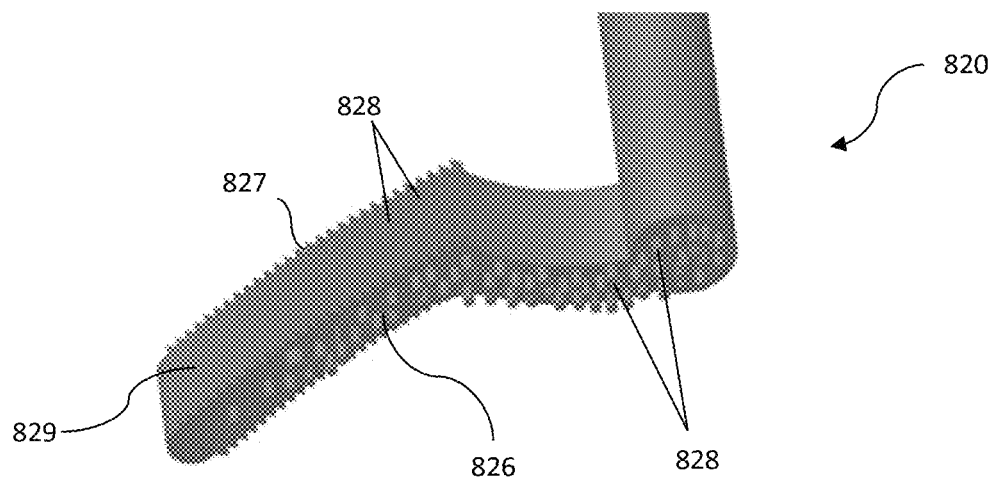
FIG. 35 is an enlarged side perspective view of a cutting structure of the chisel tool of FIG. 34.

FIGS. 31-33 show chisel tool 700 that can be used with bases 600, 600', 600", particularly during a revision surgery. Chisel 700 includes handle 710 at proximal portion 702, cutting structure 720 at distal portion 704, and shaft 715 extending between the handle and the cutting structure. Cutting structure 720 has a complementary shape to chisel slot 613, such that the cutting structure is sized and configured to fit within the chisel slot. In the illustrated embodiment, cutting structure 720 has a substantially "M" shape and includes support 722 and two prongs 724 positioned on either side of the support. Support 722 includes opposing rounded surfaces sized and configured to fit within curved portion 616 of the chisel slot 613, one surface is generally convex, and the other surface is generally concave. Each prong 724 includes opposing flat surfaces 726 that terminate at a distal surface 726, which is a substantially straight, flat cutting edge. Although in other examples, the cutting edge may include serrations, teeth, barbs, or other cutting features. Prongs 724 are sized and configured to fit within elongated portions 614 of the chisel slot 613 and are offset from a longitudinal axis of the chisel. In the illustrated embodiment, prongs 724 extend further distally than support 722, although in other examples, the support can extend the same distance as the prongs. Chisel tool 700 is designed such that cutting structure 720 can be inserted into and through chisel slots 613 to remove bone. The positioning of the chisel slots in close proximity or adjacent to ribs 670 and pegs 610 allows for removal of bone near the enhanced fixation surfaces, which enables disengagement of the ribs and the pegs for easier removal of the base component during a revision surgery.

FIG. 33 shows a system including chisel tool 700 in conjunction with base 600. As illustrated, prongs 724 are inserted through elongated portions 614 of the chisel slot 613 and support 722 is inserted in curved portion 616 of the chisel slot.

Figure 36:
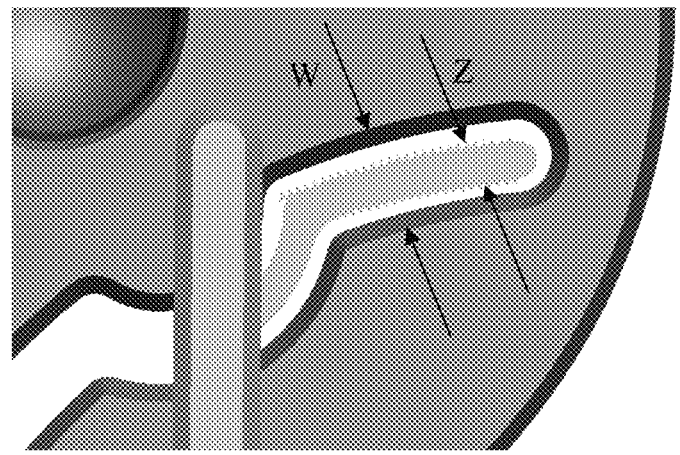
FIG. 36 is an enlarged top view of the chisel tool of FIG. 34 in conjunction with the base of FIG. 24.
Figure 37:
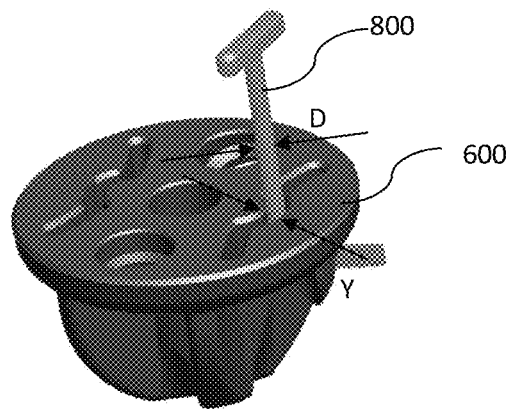
FIGS. 37-38 are side perspective views of the chisel tool of FIG. 34 in conjunction with the base of FIG. 24.
Figure 38:
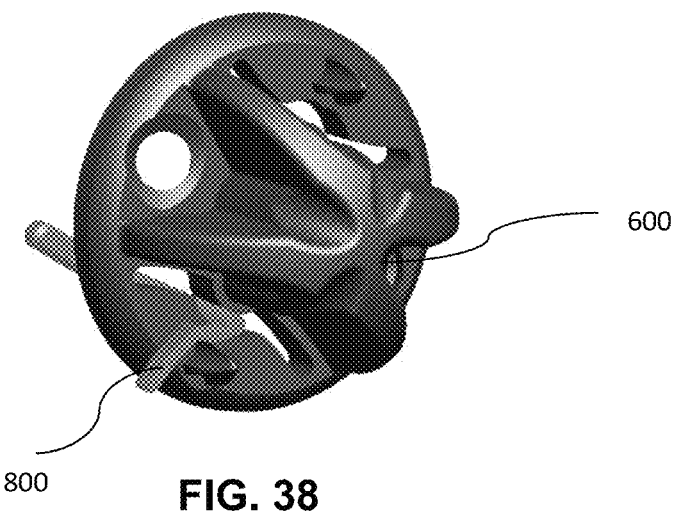

FIGS. 34-38 show another embodiment of a chisel tool 800 for use with bases 600, 600', 600". Chisel 800 includes handle 810 at proximal portion 802, cutting structure 820 at distal portion 804, and shaft 815 extending along a longitudinal axis and terminating at distal surface 817. Handle 810 can be any structure that provides a support for a surgeon to hold, and in the illustrated embodiment, the handle is a "T" bar. Handle 810 may include an impaction feature, not shown for impacting the chisel into bone. Shaft 815 is generally cylindrical and has a diameter D that is less than the width Y of the curved portion 616 of the chisel slot 613 of the base 600, as shown in FIG. 37. Cutting structure 820 extends generally transverse to the longitudinal axis of the shaft and includes curved portion 816 extending outwardly from a distal end of the shaft 815 and elongated portion 814 connected to the curved portion. Cutting structure 820 is sized and configured to fit within chisel slot 613 of base 600, such that elongated portion 814 and curved portion 816 each have a width that is less than the width of the chisel slot. Specifically, as shown in FIG. 36, elongated portion 814 of the cutting structure 820 of the chisel 800 has a width Z that is less than the width W of the elongated portion 614 of the chisel slot 613 of the base 600. In this manner, cutting structure 820 of the chisel 800 extends into and through the chisel slot 613 to remove the bone in-growth for easier removal of the base during a revision surgery.

Cutting structure 820 includes proximal surface 827, distal surface 826 opposite the proximal surface, and side walls 829 extending between the proximal and distal surfaces. Proximal surface 827, distal surface 826 and side walls 829 are substantially flat and may include a plurality of cutting members or teeth 828 projecting from each surface to aid in the cutting of bone during a revision surgery. Distal surface 817 of shaft 815 also includes teeth 828 projecting distally therefrom, and in some examples, a portion of the length or the entirety of the length of shaft 815 includes a cutting feature, such as teeth 828. The cutting features included on the proximal and distal surfaces and the side walls may be the same or different. For example, the side walls may include ridges, and the distal surface may include protrusions.

During a revision surgery, chisel tool 800 is aligned with chisel slot 613 of a base, for example base 600. For example, elongated portion 814 of chisel tool 800 is aligned with a first elongated portion 614 of a first chisel slot 613. A surgeon impacts handle 810 to drive cutting structure 820 into bone for bone removal. With cutting structure 820 extended completely through chisel slot 613, torque is applied to handle 810 to rotate the cutting structure to remove bone. The removal of the bone is facilitated and expedited by the sharp teeth 828 on the cutting structure 820. After the bone under the first chisel slot 613 is removed, the chisel tool can be used in the same manner to remove the bone under the second chisel slot of the base.

In another embodiment, two chisel tools 800 may be used together with a center guide (not shown) inserted within opening 630 of the base 600. The center guide may be impacted to remove the implant during revision surgery.

In another alternative embodiment of chisel tool 800 (not shown), the cutting structure may be symmetric about the central axis, such that the cutting structure mimics the shape of chisel slot 613, and there is an identical curved portion and elongated portion of the cutting structure on an opposing side of the shaft. In this manner, both elongated portions 614 of a first chisel slot 613 can be removed at the same time.

Figure 39:
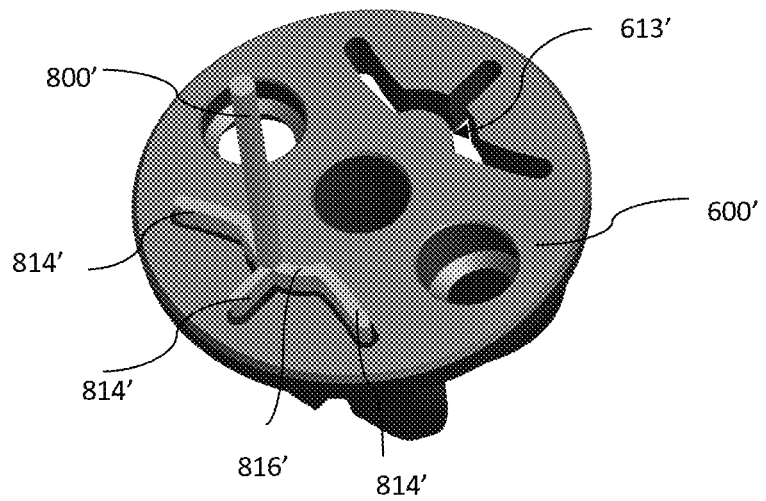
FIG. 39 is a top perspective view of a chisel tool according to another aspect of the disclosure in conjunction with the base of FIG. 29.
Figure 40:
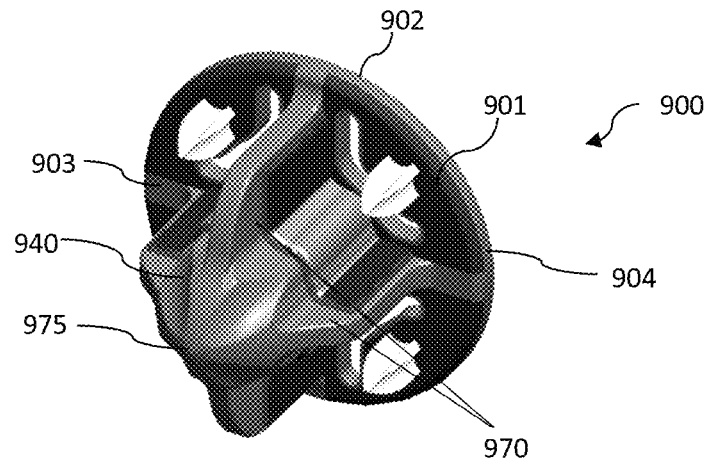
FIG. 40 is a bottom perspective view of a shoulder implant according to another aspect of the present disclosure.

FIG. 39 shows chisel tool 800' in conjunction with base 600', the chisel tool 800' is similar in most respects to chisel tool 800, the similar features of which will not be described. Chisel tool 800' has a shape complementary to chisel slot 613' of base 600'. Chisel tool 800' includes cutting structure 820' with curved portion 816' and elongated portion 814' on opposing sides of shaft 815'. Cutting structure 820' also includes central elongated portion 814' projecting from curved portion 816' sized and configured to fit into central elongated portion 614' of the chisel slot 613. Each of the elongated portions 614' and the curved portion 616' includes a cutting feature, similar to the plurality of teeth 828 of the chisel 800. In this manner, chisel tool 800' can remove bone from the entirety of the chisel slot 613' at the same time. Additionally, central elongated portion 814' allows for greater access to the bone between pegs 610', which can help to remove the bone between the pegs more easily to disengage the pegs. This can facilitate an easier removal of the base 600' during revision surgery.

FIGS. 40-43 show base 900 according to yet another aspect of the present disclosure. Base 900 is similar to bases 200 and 600, the similar components of which will not be described again. In the illustrated embodiment, base 900 includes collar 901 that is generally annularly shaped and includes rounded side wall 904 extending between bone-engaging surface 903 and proximal surface 902. Proximal surface 902 may include an opening (not shown) with a connection portion, such as a thread or taper, e.g. Morse taper, for connection to an articulating prosthetic component, such as a prosthetic humeral head, and preferably also with an instrument to facilitate the removal of the base during a revision surgery, such as by pulling out the implant or using a slap hammer.

Base 900 includes central anchor 940 extending distally from bone-engaging surface 903 and terminating at a distal end or tip 975. Distal tip 975 allows for entry of the implant into the bone, and the distal tip may be angled between about 60 degrees and about 85 degrees from a vertical axis of the central anchor 940, and preferably about 75 degrees from the vertical axis.

Figure 41:
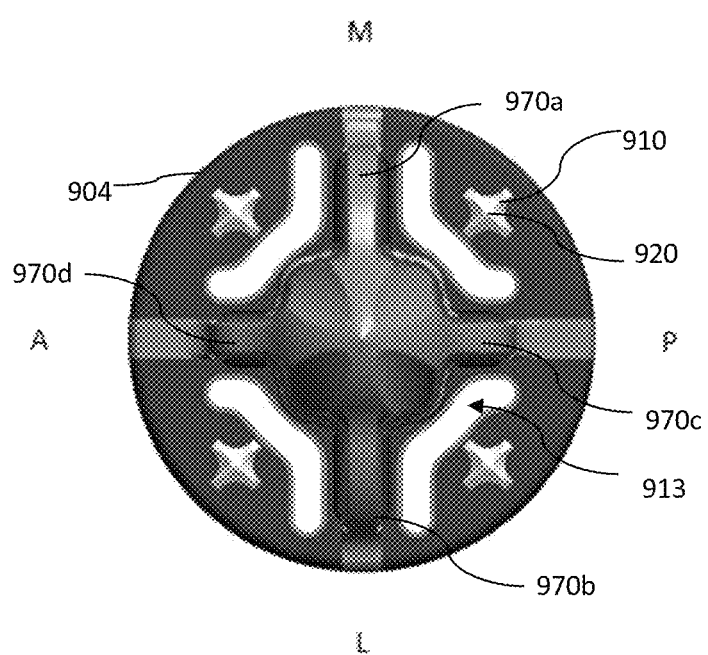
FIG. 41 is a bottom view of the base of FIG. 40.

For purposes of illustration, FIG. 41 has been labeled to show the anterior ("A"), posterior ("P"), medial ("M"), and lateral ("L") positions of base 900. Base 900 includes four ribs 970, which each corresponds to a distinct position of the base. For example, rib 970a is oriented toward the medial position, rib 970b is oriented toward the lateral position, rib 970c is oriented toward the posterior position, and rib 970d is oriented toward the anterior position. Ribs 970a and 970b, extending in the medial-lateral direction are substantially in line with one another, and ribs 970c and 970d, extending in the anterior-posterior direction are also substantially in line with each other and are substantially perpendicular to ribs 970a and 970b. As such, the ribs 970 may be said to define four quadrants of the base. Ribs 970a and 970b extend closer to side wall 904 than do ribs 970c and 970d. As such, the span across ribs 970a and 970b is greater than the diameter or span across ribs 970c and 970d. As a result, the ribs 970 have a greater span in the medial-lateral direction than in the anterior-posterior direction, as best shown in FIG. 41. Anchor 940 includes surfaces 976 extending from distal end or tip 975 to bone-engaging surface 903 and positioned between two adjacent ribs 970. Surfaces 976 are rounded and, in the illustrated embodiment, are generally convex.

Figure 42:
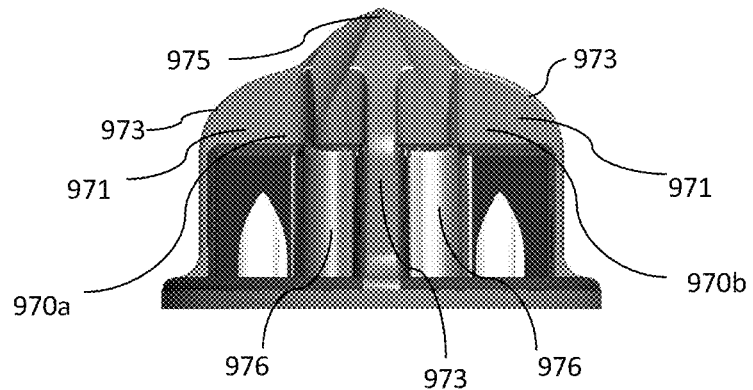
FIG. 42 is a side view of the base of FIG. 40.

Each rib 970 includes two opposing lateral side walls 971 and outer surface 973 between the two lateral side walls 971. FIG. 42 shows a side view of base 900 and more particularly shows the span of side walls 971 of the medial rib 970a and the lateral rib 970b. As shown in this view, distal tip 975 transitions into ribs 970. As distal tip 975 transitions into medial and lateral ribs 970a and 970b, respectively, outer surface 973 is generally convex. The convex shape increases the amount of material for enhanced ingrowth surface and increases the rotational stability of the base.

Figure 43:
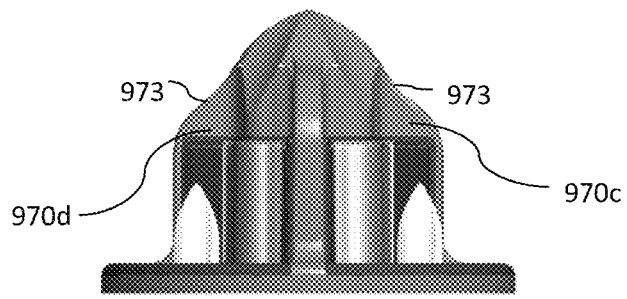
FIG. 43 is a front view of the base of FIG. 40.

FIG. 43 shows the span of the side walls 971 of the posterior rib 970c and anterior rib 970d. As shown in this view, as distal tip 975 transitions into posterior and anterior ribs 970c and 970d, respectively, outer surface 973 is generally concave, which helps to compress and accommodate bone during impaction.

Additionally, as seen in FIGS. 42-43, the width of each outer surface 973 of the ribs 970 decreases in the proximal to distal direction. As such, the width of the outer surface 973 is wider nearer to bone-engaging surface 903 than to the distal tip 975.

Collar 901 includes a plurality of continuous chisel slots 913 extending through bone-engaging surface 903 to proximal surface 902. In the illustrated embodiment, there are four chisel slots 913 with each chisel slot positioned radially outward of a surface 976 and between two adjacent ribs 970. Chisel slot 913 is positioned along a path that tracks adjacent to ribs 970 on collar 901, and the portion of each chisel slot adjacent medial and lateral ribs 970a and 970b extend further radially outward toward side wall 904 than the portion of each chisel slot that extends adjacent posterior and anterior ribs 970c and 970d. As shown in FIG. 41, each chisel slot 913 is asymmetric about at least two planes.

Collar 901 includes a plurality of peripheral anchors or pegs 910 extending distally from bone-engaging surface 903 to distal tips 920. Pegs 910 are positioned radially outwardly of chisel slots 913, and have substantially the same structure as pegs 210 described above with reference to base 200. Pegs 910 are oriented such that when the base is implanted, the pegs are fixed within the bone near the cortical rim and within the cancellous bone. With placement of the pegs 910 within good quality bone, the pegs aid in the fixation of base 900 to the bone, and may particularly assist in initial fixation. While there can be any number of pegs 910 on collar 901, preferably there are four pegs positioned at substantially equal circumferential intervals around the collar. As described in greater detail above, the use of four pegs aids in initial fixation of the implant component with bone during implantation.

Like chisel slots 613 of base 600, chisel slots 913 are sized and positioned to facilitate removal of the base during a revision procedure. With chisel slots positioned between anchor 940 and pegs 910, the chisel slots allow for loosening of the bone ingrowth on the enhanced fixation surfaces on ribs 970 and surfaces 976 as well as the bone fixed to the pegs. A chisel tool (not shown) may be similar to tool 720 but may have a correspondingly mating shape to fit within the chisel slots 913, may be used to remove the bone from the base to detach the base therefrom. Additionally, more than one chisel slot may be used at the same time. As the bone is removed from more than one chisel slot it creates a form of plug to allow the base to be removed at once. In an alternative embodiment (not shown), the chisel slots 913 may be angled to allow a tool to track along a path that closely matches or is substantially parallel to the longitudinal axis of the anchor 940. As such, the profile of the each chisel slot may be perpendicular to collar 901.

Collar 901 includes a coating forming an enhanced fixation surface that may be a porous metal surface, such as porous titanium alloy. The fixation surface may facilitate bone ingrowth after impaction and may be rougher for greater friction between the enhanced surface and bone for additional fixation. Portions of base 900 may include at least one layer of an enhanced fixation surface. In the illustrated embodiment, a portion of each side wall 971 of ribs 970 includes an enhanced fixation surface, and a portion of each surface 976 of the anchor 940 includes an enhanced fixation surface. Specifically, the portions of anchor 940 having enhanced surfaces may include three materials. A first, inner surface may be formed of solid metal, such as titanium, the second surface may be formed of a porous metal, such as a porous titanium alloy, such as Tritanium®, and a third and outer surface may be formed of a modified or directional Tritanium®. The outer surface may be formed to increase friction with the bone and may help to increase initial stability. In the illustrated embodiment, between about 30 percent and about 60 percent, and preferably between about 40 percent and about 50 percent, of the total depth of anchor 940 is solid, the depth being measured from the proximal end of the anchor to the distal end. This solid portion is in line with the punched cavity and helps to maintain alignment of the base during impaction into the punched cavity. Of course, other portions of base 900, including all or a portion of collar 901 may include one or more layers of coatings, alternatively, the entirety of the base may include surface coatings for bone ingrowth.

Figure 44:
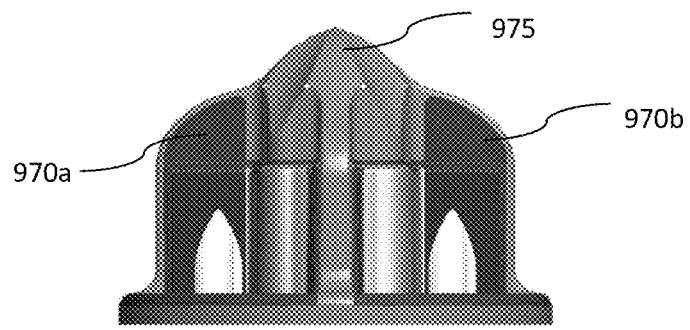
FIGS. 44-45 are side views of an alternative embodiment of the base of FIG. 40.
Figure 45:
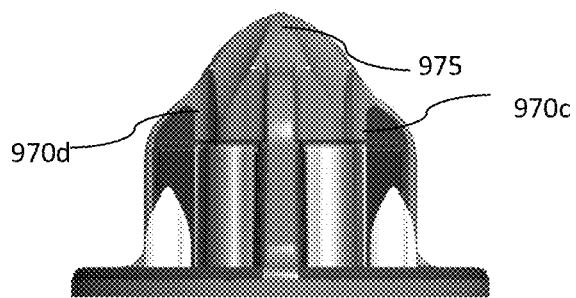
Figure 46:
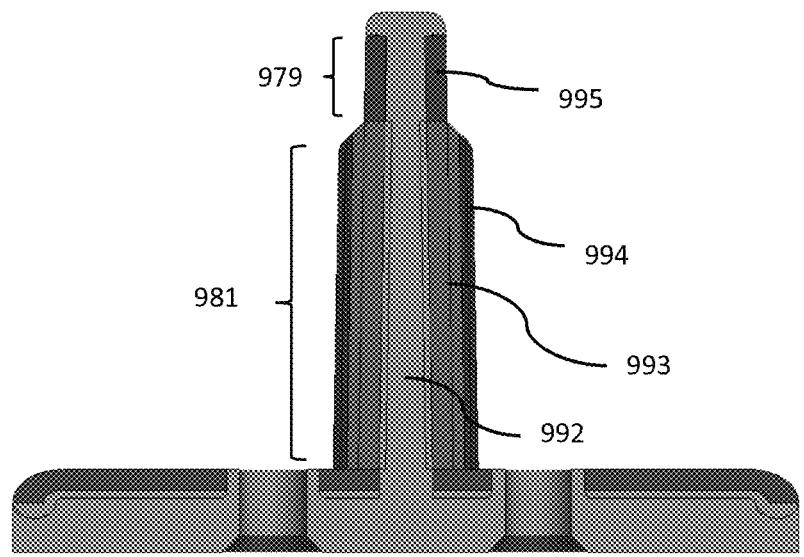
FIG. 46 is a cross-sectional view showing the surfaces of the base of FIGS. 44-45.

In another alternative embodiment, as shown in FIGS. 44-46, anchor 940 of base 900 includes a distal portion of enhanced fixation surface on side walls 971 of ribs 970 that includes a porous metal, such as a porous titanium alloy, such as Tritanium®. FIG. 46 shows the distal portion 979 of the ribs having a coating surface 995 of a porous metal, such as porous titanium alloy, such as Tritanium® on a solid metal. The portion 981 proximal to distal portion 979 includes a first, inner surface 992 of solid metal, a second surface 993 of a porous metal, such as a porous titanium alloy, and the third, outer surface 994 of modified or directional porous metal. Although other arrangements of surface coatings are contemplated.

Figure 47:
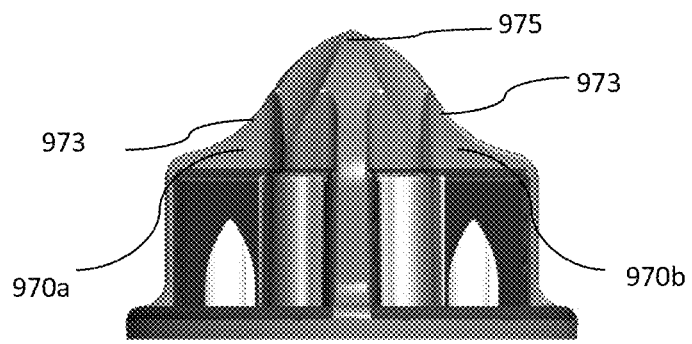
FIG. 47 is a side view of another alternative embodiment of the base of FIG. 40.

In yet another alternative embodiment, as shown in FIG. 47, as distal tip 975 transitions into each of the ribs 970, including medial and lateral ribs 970a and 970b, outer surface 973 is generally concave. The concavity of the outer surface 973 of the ribs 970 is designed to accommodate the bicipital groove and maintain a distance therefrom.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A base member of a stemless shoulder implant, the base member comprising:
a proximal collar having a main proximal surface and a bone-engaging surface opposite the proximal surface, wherein the proximal collar is annular and defines a continuously circular outer surface and a continuously circular inner surface;
an anchor extending distally from the bone-engaging surface of the collar;
a central opening in the proximal collar, the central opening having a taper, the central opening shaped and sized to receive a tapered connector of a prosthetic humeral head to lock the prosthetic humeral head to the base; and
an annular rim that defines a continuously circular outer surface that is positioned radially inward of the continuously circular inner surface of the proximal collar, the central opening being positioned radially inward of the continuously circular inner surface of the annular rim,
wherein a cylindrical recess is defined between the continuously circular inner surface of the proximal collar and the continuously circular outer surface of the annular rim,
wherein an entirety of the cylindrical recess has a depth extending distally of a distal-most surface of the bone-engaging surface of the proximal collar.

2. The base member of claim 1, wherein a proximal end of the annular rim is flush with the main proximal surface of the proximal collar.

3. The base member of claim 1, wherein a distal end of the central opening terminates in a proximal end of the anchor.

4. The base member of claim 3, wherein the anchor extends from the proximal end of the anchor to a tip at a distal end of the anchor.

5. The base member of claim 4, wherein the anchor is solid from the proximal end of the anchor to the tip at the distal end of the anchor.

6. The base member of claim 1, wherein the proximal collar includes a plurality of arcuate apertures.

7. The base member of claim 6, wherein the plurality of arcuate apertures includes four arcuate apertures.

8. The base member of claim 7, wherein the plurality of arcuate apertures are spaced equidistantly from the central opening.

9. The base member of claim 8, wherein the proximal collar includes a plurality of additional apertures positioned so that each of the plurality of arcuate apertures is positioned radially between one of the plurality of additional apertures and the central opening.

10. The base member of claim 1, wherein the anchor includes four ribs, each of the four ribs having a first end extending from the bone engaging surface of the proximal collar, the four ribs converging to a tip at the distal end of the anchor.

11. The base member of claim 10, wherein the tip at the distal end of the anchor is positioned along a center longitudinal axis of the base, the center longitudinal axis passing through the central opening.

12. The base member of claim 11, wherein each of the four ribs is spaced 90 degrees from a circumferentially adjacent one of the four ribs.

13. The base member of claim 12, wherein each of the four ribs includes two opposing lateral side walls, and an outer surface between the two opposing lateral side walls.

14. The base member of claim 13, wherein the two opposing lateral side walls of each of the four ribs includes porous metal to form an enhanced fixation surface on the two opposing lateral side walls.

15. The base member of claim 14, wherein the bone-engaging surface of the proximal collar includes porous metal to form an enhanced fixation surface on the bone engaging surface of the proximal collar.

* * * * *